US006214988B1

(12) United States Patent
Lukasavage et al.

(10) Patent No.: US 6,214,988 B1
(45) Date of Patent: Apr. 10, 2001

(54) PROCESS FOR MAKING AN HMX PRODUCT

(75) Inventors: William J. Lukasavage, Pearland; Lawrence A. Behrmann, Houston, both of TX (US); Wallace E. Voreck, Sparta, NJ (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 09/476,947

(22) Filed: Jan. 3, 1999

Related U.S. Application Data

(60) Provisional application No. 60/135,970, filed on May 26, 1999.

(51) Int. Cl.$^7$ .................................................. C07D 257/02

(52) U.S. Cl. ........................ 540/47.5; 540/470; 540/474

(58) Field of Search .................................... 540/475, 470, 540/474

(56) References Cited

U.S. PATENT DOCUMENTS

| | | | |
|---|---|---|---|
| H50 | 4/1986 | Surapaneni et al. ................. | 260/239 |
| 2,434,230 | 1/1948 | Schiessler et al. ................... | 260/248 |
| 2,656,355 | 10/1953 | Bachmann .......................... | 260/248 |
| 2,798,102 | 7/1957 | Schaeffer et al. ................... | 260/674 |
| 2,959,587 | 11/1960 | Johnson et al. ..................... | 260/248 |
| 3,030,376 | 4/1962 | Liggett et al. ...................... | 260/309 |
| 3,304,300 | 2/1967 | Watters .............................. | 260/239 |
| 3,673,174 | 6/1972 | Smith et al. ........................ | 260/239 |
| 3,939,148 | 2/1976 | Siele et al. ......................... | 260/239 |
| 3,979,379 | 9/1976 | Siele .................................. | 260/239 |
| 4,048,167 | 9/1977 | Paul et al. ........................... | 544/215 |
| 4,638,062 | 1/1987 | Kronenthal ......................... | 540/355 |
| 4,638,065 | 1/1987 | Svensson et al. ................... | 544/196 |
| 5,120,887 | 6/1992 | Lukasavage et al. ............... | 568/924 |
| 5,124,493 | 6/1992 | Lukasavage et al. ............... | 568/924 |
| 5,212,308 | 5/1993 | Lukasavage et al. ............... | 544/215 |
| 5,246,671 | 9/1993 | Lukasavage et al. ............... | 422/111 |
| 5,250,687 | 10/1993 | Lukasavage et al. ............... | 544/215 |
| 5,268,469 | 12/1993 | Lukasavage et al. ............... | 540/475 |
| 5,355,802 | 10/1994 | Petitjean ............................. | 102/313 |
| 5,505,134 | 4/1996 | Brooks et al. ...................... | 102/203.7 |
| 5,597,974 | 1/1997 | Voreck, Jr. et al. ................. | 102/307 |
| 5,673,760 | 10/1997 | Brooks et al. ...................... | 175/4.6 |
| 5,682,004 | 10/1997 | Fels et al. ........................... | 86/21 |
| 5,739,325 | 4/1998 | Wardle et al. ...................... | 540/554 |
| 5,750,920 | 5/1998 | Redecker et al. ................... | 149/11 |
| 5,780,644 | 7/1998 | Gozzini et al. ..................... | 548/478 |
| 5,874,574 | 2/1999 | Johnston et al. .................... | 540/475 |
| 5,911,277 | 6/1999 | Hiromas et al. .................... | 166/297 |

FOREIGN PATENT DOCUMENTS 36 14 173 C1    3/1989  (DE) .

OTHER PUBLICATIONS

Bellamy, "Nitrolysis of TAT and DADN with $N_2O_5/HNO_3$: Formation of α–HMX," *Energetic Materials Production, Processing and Characterization*, $29^{th}$ International Conference of ICT (Jun. 30–Jul. 3, 1998).
Siele et al., "The Preparation of 3,7–Diacyl–1,3,5,7–tetraazabicyclo[3.3.1] Nonanes," *Notes* 11:237–239 (1974).
Wright, "Methods of Formation of the Nitramino Group, Its Properties and Reactions," Chap. 9, pp. 613–684.
Ju et al., "Study on the Mechanism of the Acetolysis of Hexamethylenetetramine," *Propellants, Explosives, Pyrotechnics* 15:54–57 (1990).
Ju et al., "Use of NMR Spectrometry for Studying the Acetolysis of Hexamethylenetetramine. I. The Reaction of TAT Formation from DAPT," *Propellants, Explosives, Pyrotechnics* 9:58–63 (1984).
Shaofang et al., "Use of NMR Spectrometry for Studying the Acetolysis of Hexamethylenetetramine III. The Reaction between Hexamethylenetetramine and Acetic Anhydride to Form TRAT," *Propellants, Explosives, Pyrotechnics* 12:41–45 (1987).
Cooney et al., "Nitrogen–15 Studies of the Mechanisms of Acetolyses of Hexamethylenetetramine and 3,7–Diacetyl–1, 3,5,7–Tetraazabicyclo[3.3.1]Nonane(DAPT)," *J. Heterocyclic Chem.* 24:1163–1167 (1987).
Bachmann et al., "Cyclic and Linear Nitramines Formed by Nitrolysis of Hexamine," Chemistry Laboratory of the University of Michigan, pp. 2769–2773 (1951).
Chem. Abstract 80:49973k (1973).
Chem. Abstract 82:171118s (1974).
Chem. Abstract 84:180317z (1976).
Chem. Abstract 86:16714x (1976).
Chem. Abstract 86:72719q (1976).
Chem. Abstract 89:62015e (1978).
Chem. Abstract 120:138736x (1993).

(List continued on next page.)

*Primary Examiner*—Mukund J. Shah
*Assistant Examiner*—Pavanaram K. Sripada
(74) *Attorney, Agent, or Firm*—Williams Morgan & Amerson P.C.

(57) ABSTRACT

A process for preparing an HMX product comprises the steps of:
  (a) providing a granule that comprises a plurality of alpha-HMX particles and which has internal void spaces; and
  (b) sorbing at least one second material into the void spaces in the granule.

The second material can be sorbed into the granules by using a vacuum to draw a gas phase comprising the second material into the granule. Alternatively, the second material can be sorbed into the granules by dissolving or dispersing the second material in a liquid solvent, contacting the solvent with the granules, and evaporating the solvent, whereby the second material is sorbed into the granules. Various second materials can be used, such as energetic materials and fuels.

24 Claims, 2 Drawing Sheets

OTHER PUBLICATIONS

Chem. Abstract 100:123574f (1983).
Chem. Abstract 113:135227b (1990).
Chem. Abstract 114:105257q (1990).
Chem. Abstract 117:111657y (1992).
Chem. Abstract 117:93183j (1992).
Chem. Abstract 49:7606, "Nitramines" (1954).
Chem. Abstract 58:5448, "Fine–Grained HMX" (1962).
Chem. Abstract 60:14328, "Explosive Compositions Containing Oxidizing Agents and Metals" (1964).
Chem. Abstract 61:3128, "Processing of HMX" (1964).
Chem. Abstract 66:39499g (1966).
Chem. Abstract 66:67516d (1967).
Chem. Abstract 66:77932a (1967).
Chem. Abstract 66:106754b (1967).
Chem. Abstract 53:22956, "Separation of Cyclotetramethylenetetranitramine from Cyclotrimethylenetrinitramine" (1959).
Chem. Abstract 54:20211, "Preparation of HMX by Using Boron Trifluoride" (1960).
Chem. Abstract 55:20436, "Homocyclonite" (1961).
Chem. Abstract 98:163352d (1982).
Chem. Abstract 99:73150c (1982).
Chem. Abstract 101:191980f (1984).
Chem. Abstract 102:134424z (1983).
Chem. Abstract 104:71281u (1985).
Chem. Abstract 105:229374j (1985).
Chem. Abstract 106:35607n (1986).
Chem. Abstract 106:35608p (1986).
Chem. Abstract 106:35610h (1986).
Chem. Abstract 106:52780f (1986).
Chem. Abstract 106:158922u (1986).
Chem. Abstract 107:238899c (1987).
Chem. Abstract 107:99291h (1987).
Chem. Abstract 108:111519u (1987).
Chem. Abstract 108:43280g (1987).
Chem. Abstract 108:23707y (1987).
Chem. Abstract 108:23708z (1987).
Chem. Abstract 108:166755y (1987).
Chem. Abstract 110:135274c (1987).
Chem. Abstract 110:60614c (1988).
Chem. Abstract 110:60615d (1988).
Chem. Abstract 111:226752u (1988).
Chem. Abstract 113:26444z (1990).
Chem. Abstract 114:6469d (1988).
Chem. Abstract 114:170455s (1990).
Chem. Abstract 114:164190k (1991).
Chem. Abstract 115:262544u (1991).
Chem. Abstract 116:258591k (1991).
Chem. Abstract 118:15654v (1992).
Chem. Abstract 118:172045q (1993).
Chem. Abstract 119:52482d (1993).
Chem. Abstract 123:117652p (1995).
Chem. Abstract 123:286108w (1994).
Chem. Abstract 123:344956j (1995).
Chem. Abstract 124:347528c (1995).
Chem. Abstract 125:172529v (1996).
Chem. Abstract 126:279785y (1997).
Chem. Abstract 127:250218a (1996).
Chem. Abstract 128:142778v (1997).
Chem. Abstract 129:124494r (1988).
Chem. Abstract 94:142100x (1979).
Chem. Abstract 95:172015m (1980).
Chem. Abstract 95:7242a (1980).
Chem. Abstract 95:222345s (1981).
Chem. Abstract 95:222346t (1981).
Chem Abstract 96:8904a (1981).
Chem. Abstract 96:68958f (1980).
Chem. Abstract 97:130024z (1981).
Chem. Abstract 98:80485y (1983).
Chem. Abstract 43:8354, "The Nitrolysis of Hexamethylenetetramine. I. The Significance of 1,5–endomethylene–3,7–dinitro–1,3,5,7–tetrazacyclooctane" (1949).
Chem. Abstract 43:9072, "Nitrolysis of Hexamethylenetetramine. II. Nitrolysis of 1,5–endomethylene–3,7–dinitro–1,3,5,7–tetrazacyclooctane (DPT)" (1949).
Chem. Abstract 43:9075, "Recombination of Fragments During Hexamethylenetetramine Nitrolysis in Acetic Anhydride" (1949).
Chem. Abstract 43:9079, "Nitramines" (1949).
Chem. Abstract 44:1117, "The Preparation of Octogen (Cyclotetramethylenetetranitramine)" (1949).
Chem. Abstract 46:2084, "Cyclic and Linear Nitramines Formed by Nitrolysis of Hexamine" (1951).
Chem. Abstract 46:2085, "Structure Determination and Synthesis of 1–Acetamidomethylhexamine Nitrate" (1951).
Chem. Abstract 46:2085, "The Nitrosation of Hexamethylenetetramine and Related Compounds" (1951).
Chem. Abstract 47:9983, "RDX and HMX Production in the Bachmann Reaction" (1952).
Chem. Abstract 50:15113, "Development of HMX for Utilization in Powerful Explosives" (1963).
Chem. Abstract 63:8387, "Octogen" (1965).
Chem. Abstract 64:15755, "Single Stage Process of the Preparation of Cyclotetramethylenetetranitramine" (1964).
Chem. Abstract 64:19616, "Chemistry of Nitramines. III. Cyclic Nitramines Derived from Trimethylenedinitramine" (1966).
Chem. Abstract 66:20689x (1966).
Chem. Abstract:11915, "Purification of Cyclotetramethylenetetranitramine" (1963).
Chem. Abstract 66:4559k (1966).
Chem. Abstract 67:75044j (1966).
Chem. Abstract 68:39192t (1967).
Chem. Abstract 69:32007y (1968).
Chem. Abstract 70:10960x (1967).
Chem. Abstract 70:116764b (1967).
Chem. Abstract 71:91449h (1969).
Chem. Abstract 71:50009w (1968).
Chem. Abstract 71:126700n (1969).
Chem. Abstract 72:68810f (1969).
Chem. Abstract 73:68153q (1970).
Chem. Abstract 76:85850u (1971).
Chem. Abstract 77:62040m (1972).
Chem. Abstract 82:19165x (1974).
Chem. Abstract 83:118022a (1974).
Chem. Abstract 120:221771a (1993).
Chem. Abstract 121:107806m (1994).
Chem. Abstract 43:8137, "A New Method of Preparing the High Explosive RDX" (1949).
Chem. Abstract 41:6105, "X–Ray Diffraction Patterns for the Identification of Crystalline Constituents of Explosives" (1947).
Chem. Abstract 43:4855, "The Sensitiveness of Solid High Explosives to Impact" (1948).

US 6,214,988 B1

PROCESS FOR MAKING AN HMX PRODUCT

CROSS-REFERENCE TO RELATED APPLICATION

This patent application claims benefit of U.S. provisional application 60/135,970, filed on May 26, 1999.

FIELD OF THE INVENTION

The invention relates to processes for producing HMX (1,3,5,7-tetranitro-1,3,5,7-tetraazacyclooctane), processes for producing intermediates that can be used to produce HMX, and compounds and compositions produced by various of these processes.

BACKGROUND OF THE INVENTION

HMX (1,3,5,7-tetranitro-1,3,5,7-tetraazacyclooctane), also referred to as octogen or cyclotetramethylenetetranitramine, is a highly energetic material that is useful in various explosives and propellants for military and non-military applications. HMX is recognized as one of the most powerful nitramine explosives, and is used as the benchmark for all other explosives.

HMX is known to exist in four different crystal structures or polymorphic forms—alpha, beta, gamma and delta. Of these polymorphs, it was long believed that the beta form was the least sensitive and most stable, and thus the beta polymorph has been the most widely used form of HMX. The alpha and gamma polymorphs have commonly been dismissed as too dangerous for use due to greater sensitivity, and the delta polymorph is so unstable that it is of no commercial significance.

Despite its superior energetic properties, HMX has not been widely used as an explosive due to difficulties in large-scale production and excessive manufacturing costs. The first known process for the manufacture of HMX, the Bachmann process, was developed in the 1940's. The Bachmann process involves nitrolysis of hexamine (also known as hexamethylenetetraamine) with a mixture of nitric acid and a large excess (e.g., 20-fold) of acetic anhydride. HMX is produced as a by-product or contaminant along with a greater amount of another explosive, RDX (hexahydro-1,3,5-trinitro-1,3,5-triazine). The Bachmann process typically provides yields of 80–84%, of which only about 10–40% is HMX, based on the methylene content of the feed. When fully optimized for HMX, the maximum reported yield of HMX per mole of hexamine feed is about 64%. Due to the inefficiencies in the process, and the large amounts of hazardous waste materials produced, it is not appropriate for large-scale industrial production.

Other synthetic routes for making HMX have been proposed, involving various intermediates. One such intermediate that has been used to produce HMX is DAPT (3,7-diacetyl-1,3,5,7-tetraazabicyclo-[3.3.1]-nonane). DAPT is generally made by reaction of wet hexamine and acetic anhydride. One problem common to all methods of manufacturing DAPT is the massive amount of heat generated by the reaction. Because DAPT in solution will decompose rapidly at temperatures ranging from about 20–120° C., depending on pH, it is necessary to remove heat from the reaction mixture and thus keep the temperature low. In effect, the rate of DAPT production is typically limited by the capacity of the reaction apparatus to withdraw heat by means of heat exchangers or the like. Due to the extremely exothermic nature of this reaction, in practice the rate of addition of acetic anhydride to the hexamine has been kept very low, so the rate of heat generation is kept at manageable levels. As a result, the time required to synthesize a given amount of DAPT is quite long, and the cost is relatively high. One method proposed for dealing with the tremendous amounts of heat generated by the reaction is to mix ice and water with hexamine to create a slurry, and then add acetic anhydride to the slurry. (Lukasavage U.S. Pat. No. 5,246,671.) Suitable temperatures for this reaction slurry are described as ranging from −18° C. up to 120° C.

Another intermediate that can be used in the production of HMX is TAT (1,3,5,7-tetraacetyl-1,3,5,7-tetraazacyclooctane, also known as 1,3,5,7-tetraacetyloctahydro-1,3,5,7-tetrazocine). TAT can be prepared by heating DAPT with acetic anhydride under anhydrous conditions, but the yields from this process have been poor. Another process used to prepare TAT involves reacting DAPT with acetic anhydride, acetyl chloride, and an alkanoic acid salt such as sodium acetate, under anhydrous conditions. (Siele U.S. Pat. No. 3,979,379.) However, this process uses a large excess of acetic anhydride, thus making it relatively expensive. Yet another process that has been used to make TAT involves reacting DAPT with acetic anhydride in the presence of a metal acetate under anhydrous conditions at temperatures of 100–125° C. (Surapaneni U.S. Statutory Invention Registration H50.) However the reaction conditions and yield that have been reported for this process indicate that it is not economical for commercial use.

HMX can be synthesized by nitrolysis of TAT, using nitric acid and dinitrogen pentoxide or phosphorous pentoxide, at temperatures ranging from room temperature up to 400C. (Lukasavage U.S. Pat. Nos. 5,124,493 and 5,268,469.) This process too, however, has not seen acceptance on a large production scale due to the economics involved.

SOLEX (1-(N)-acetyl-3,5,7-trinitro-cyclotetramethylenetetramine) is another nitra ine explosive, which is a byproduct of the nitration of TAT to form HMX. SOLEX is relatively stable, having twice the impact resistance of RDX, is easily isolated, and can be produced using far less nitrating agent than is required for the direct preparation of HMX from TAT.

One process that has been described for the production of SOLEX involves adding TAT to a solution of 98% nitric acid and phosphorus pentoxide at a temperature between 20–45° C. (Lukasavage U.S. Pat. No. 5,120,887.) The purity and product yields from this method are reported to be quantitative. Significantly, however, this method requires an excess of nitrating agent, i.e., 7.5 grams of nitric acid per gram of TAT used, which makes the process relatively expensive. The SOLEX can be converted to HMX by treatment with strong nitric acid.

Beta-HMX has been widely used as an explosive, despite the difficulties and expense involved in its manufacture. One specific form that is sold is referred to as Class 5 beta-HMX (defined as particulate beta-HMX of which 98% by weight will pass a 325 mesh (44 $\mu$m) sieve). Class 5 beta-HMX can be sold for a higher price than coarser beta-HMX products, but is also more difficult to make. Usually it is made by first forming larger beta-HMX particles, and then either grinding them in a water slurry or "sand blasting" them against a hard surface, whereby the desired finer beta-HMX particles are produced. This procedure is troublesome and relatively expensive.

Recently it was discovered that alpha-HMX can be produced that exhibits less sensitivity to impact than beta- HMX. (Lukasavage U.S. Pat. No. 5,268,469.) Production of this polymorph at a reasonable cost on a large scale would be advantageous as it would be useful as a substitute for the beta-HMX used in existing explosive formulations.

Another problem in the prior art involves making durable shaped articles that contain explosive materials. Such articles typically comprise both an explosive substance and a binder, the latter giving the composition the physical characteristics needed to retain the desired shape. However, such binders or other additives dilute the explosive power.

A long-standing need exists for an improved process for making HMX, and improved HMX compositions and articles that exhibit desirable stability, impact sensitivity, and explosive properties. A particular need exists for an improved process for making alpha-HMX that is relatively impact-insensitive.

SUMMARY OF THE INVENTION

One aspect of the invention is a process for making a 3,7-dialkanoyl- 1,3,5,7-tetraazabicyclo-[3.3.1]-nonane. The process comprises the steps of:

(a) dissolving hexamine in water, thereby forming a reaction mixture having a temperature of about 0–30° C. (preferably about 10–25° C., most preferably about room temperature (about 22° C.));

(b) cooling the reaction mixture to keep its temperature below about 20° C.; and (c) adding to the reaction mixture an alkanoic acid anhydride having the formula $(RCO)_2O$, where R is straight chain or branched alkyl having 1–5 carbon atoms, whereby a product solution comprising a compound having the formula

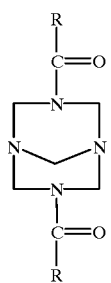

(I)

is produced, and wherein R is as defined above. Preferably in step (b), the reaction mixture is cooled to a temperature between about –30 and 10° C., more preferably between about –15 and 5° C., most preferably at or below about 0° C.

In one preferred embodiment of this process, the alkanoic acid anhydride is acetic anhydride and the product solution comprises DAPT. It is preferred to use about 2.0–2.5 moles of acetic anhydride per mole of hexamine, most preferably about 2.0–2.1 moles of acetic anhydride per mole of hexamine.

One preferred way of cooling the reaction mixture is to use an external cooling jacket through which a heat transfer fluid flows. Another way of cooling the reaction mixture involves the addition of ice (e.g., at least about 0.2 g of ice per g of hexamine). It is preferred to add about 0.2–5.0 grams of ice to the reaction mixture per gram of hexamine (more preferably about 0.2–1.0, most preferably about 0.5), and to use about 0.5–1.5 grams of water in step (a) per gram of hexamine (most preferably about 1.0 gram of water per gram of hexamine).

The ice preferably is present in an amount sufficient to maintain the temperature of the reaction mixture at a temperature between about –30° C. and about 10° C., more preferably in an amount sufficient to maintain the temperature of the reaction mixture at between about –15° C. and about 5° C., most preferably at or below about 0° C. The ice can be used in any of a variety of forms, such as crushed ice, shaved ice, block ice, and mixtures of ice and water.

Optionally, at least some of the ice or other device to provide cooling can be enclosed in a container that prevents physical contact between it and the reaction mixture, but permits heat transfer with the reaction mixture. For example, the container can be a flexible bag made of one or more thermoplastic polymers, or a rigid enclosure made of one or more thermoplastic or thermosetting polymers.

As another option, the ice can be pre-cooled to a temperature below about 0° C. before being added to the reaction mixture, preferably to a temperature below about –10° C., most preferably to below about –30° C.

As alternatives to an external cooling jacket or addition of ice, cooling of the reaction mixture can be provided by cooling coils having a heat transfer fluid flowing therethrough, thermal control rods, and the like.

The product solution in this process will typically comprise some volatile compounds. One method of removing such volatile compounds comprises the further steps of:

(d) heating the solution to at least about 40° C. and contacting the solution with a flow of air that is substantially saturated with water vapor; and (e) when about 50–80% by weight of the product solution has been evaporated, heating the solution to about 70–150° C. and continuing to contact the solution with a flow of air.

The pH of the product solution preferably is maintained above about 6.5 during steps (d) and (e), more preferably above about 7.0. In a preferred embodiment of these purification steps, the product solution is heated to about 40–45° C. in step (d), and to about 130–140° C. in step (e).

Another way of removing such volatile compounds comprises the additional steps of (d) feeding a liquid stream that comprises the product solution into the upper half of a stripper column; (e) feeding a gas stream having a temperature of at least about 120° C. into the lower half of the stripper column, whereby the gas stream and the liquid stream come into countercurrent contact in the stripper column; (f) withdrawing a stream comprising the compound having the formula (I) from the bottom of the stripper column; and (g) withdrawing a waste stream comprising air and one or more of water vapor, water, formaldehyde, and acetic acid, from the top of the column. In one embodiment, the temperature of the gas stream is about 120–130° C. In other embodiments, the temperature of the gas stream is greater than about 150° C., or even greater than about 200° C. Preferably the gas stream consists essentially of air, and the stripper column comprises packing.

This method of removing the volatile compounds can be considered to provide thermal dissociation of the DAPT salt (e.g., DAPT acetate) that enters the upper part of the stripper column, thereby forming an acid and a base. The stripper column can optionally be operated at reduced (e.g., subatmospheric) pressure and temperature.

One particularly preferred embodiment of this process can be used to make DAPT, and comprises the steps of:

(a) dissolving hexamine in water, at a ratio of about 1.0 gram of water per gram of hexamine, at a temperature of about 10–30° C., thereby forming a reaction mixture;

(b) adding ice to the reaction mixture in an amount sufficient to maintain the reaction mixture at or below about 0° C.;

(c) adding about 2.0–2.1 moles of acetic anhydride per mole of hexamine to the reaction mixture, whereby a product solution comprising DAPT and volatile compounds is produced;

(d) feeding a liquid stream that comprises the product solution into the upper half of a stripper column;

(e) feeding a gas stream having a temperature of at least about 120° C. into the lower half of the stripper column, whereby the gas stream and the liquid stream come into countercurrent contact in the stripper column;

(f) withdrawing a stream comprising the compound having the formula (I) from the bottom of the stripper column; and (g) withdrawing a waste stream comprising air and one or more of water vapor, water, formaldehyde, and acetic acid, from the top of the column.

The various embodiments of the above-described process can be operated safely with much greater throughput than prior processes. This process is especially valuable for producing DAPT. The increased production rate possible with this process significantly reduces the cost of producing DAPT.

A second aspect of the invention is a process for making a 1,3,5,7-tetraalkanoyl-1,3,5,7-tetraazacyclooctane. This process comprises the steps of:

(a) reacting a compound having the formula

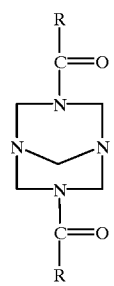

(I)

wherein R is straight chain or branched alkyl having 1–5 carbon atoms, with an alaoic acid anhydride having the formula $(RCO)_2O$, where R is as defined above, or an alkanoic acid halide (such as acetyl chloride) having the formula $RC(O)X$, where R is as defined above and X is halide, thereby producing a compound having the formula:

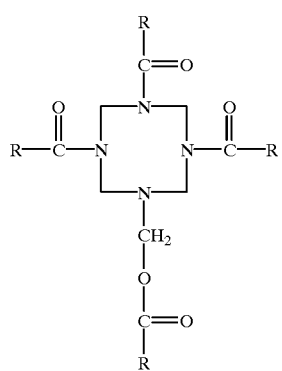

(II)

wherein R is as defined above; and (b) reacting the compound having the formula (II) with the alkanoic acid anhydride in the presence of water and a catalytic amount of at least one transition metal oxide, thereby producing a compound having the formula

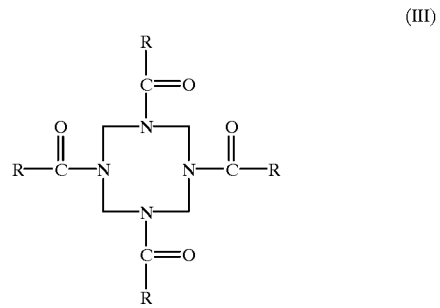

(III)

where R is as defined above.

In a preferred embodiment of this process, each R group is methyl, the alkanoic acid anhydride is acetic anhydride, and the product of step (b) comprises TAT. It is also preferred to use transition metal oxide catalysts selected from the group consisting of copper oxides, iron oxides, and mixtures thereof.

Preferably about 2.0–2.5 moles of alkanoic acid anhydride are used per mole of the compound having the formula (I), more preferably about 2.0–2.2 moles of allanoic acid anhydride per mole of that compound. It is also preferred to use about 1.0–3.0 moles of water per mole of the compound having the formula (II).

Step (a) preferably is performed at a temperature below about 138° C. Most preferably, step (a) is performed at a temperature of about 110–120° C., and subsequently the temperature is raised to about 130–140° C. for a time sufficient to evaporate residual water, alkanoic acid anhydride, and other volatile compounds.

One specific embodiment of this process makes TAT, and comprises the steps of:

(a) reacting DAPT with acetic anhydride, thereby producing a compound having the formula:

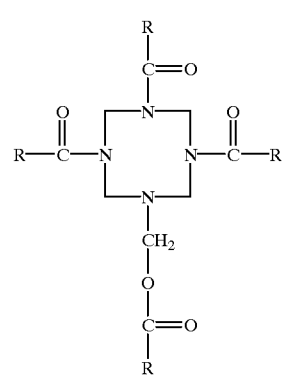

(II)

wherein R is methyl; and (b) reacting the compound having the formula (II) with acetic anhydride in the presence of water and a catalytic amount of at least one transition metal oxide, thereby producing TAT.

Another embodiment is a process for making TAT that comprises the steps of the steps of: (a) reacting DAPT with acetic anhydride; and (b) reacting the product of step (a) with acetic anhydride in the presence of a catalytic amount of at least one transition metal oxide. Preferably the product of step (b) comprises TAT, and the process also includes the step of reacting TAT with nitric acid and either phosphorus pentoxide or dinitrogen pentoxide, thereby forming Hi.

This process requires much less anhydride than prior processes, and therefore is more cost-effective.

A third aspect of the invention relates to a novel intermediate that can be used to make HMX, and a process for making that intermediate.

The novel intermediate is a compound having the formula

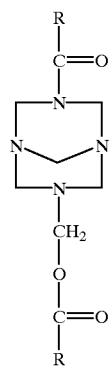

(IV)

wherein R is straight chain or branched alkyl having 1–5 carbon atoms. One such compound is 1-acetyl,5-acetate hexamethylene tetraamine (AAHT).

A process for making such an alkanoyl alkanoate hexamethylene tetraamine comprises the step of:
(a) adding an alkanoic acid anhydride having the formula (RCO)$_2$O, where R is straight chain or branched alkyl having 1–5 carbon atoms, to a slurry of hexamine and water, the slurry having a temperature between about −78° C. and about 0° C., whereby an alkanoyl alkanoate hexamethylene tetraamine is produced.

In the presently preferred embodiment of this process, R is methyl, the alkanoic acid anhydride is acetic anhydride and the alkanoyl alkanoate hexamethylene tetra mine is AAHT.

In one embodiment, the slurry can furter comprise ice. It is preferred that the temperature of the slurry of hexamnine, ice, and water is between about −50° C. and about −100° C., most preferably no higher than about −30° C. Preferably about 1.0–2.5 moles of alkanoic acid anhydride are added per mole of hexamine, most preferably about 1.0–2.2 moles of alkanoic acid anhydride per mole of hexamine.

The slurry of hexamine, ice, and water can suitably be formed by dissolving hexamine in water, and subsequently adding ice in an amount sufficient to lower the temperature of the slurry to at least about −10° C. Preferably the ice is added in an amount sufficient to lower the temperature of the slurry to at least about −30° C. Optionally the ice can be pre-cooled to at least about −30° C. prior to being added to the hexamine and water. Preferably the slurry comprises about 1–5 grams of hexamine per gram of ice, most preferably about 3 grams of hexamine per gram of ice.

One specific embodiment is a process for making AAHT that comprises the steps of:
(a) dissolving hexamine in water, thereby forming a hexamine solution;
(b) forming a slurry of hexamine, ice, and water by adding ice that has been pre-cooled to at least about −30° C. to the hexamine solution, the ice being added in an amount sufficient to lower the temperature of the slurry to at least about −10° C.; and
(c) adding acetic anhydride to the slurry of hexamine, ice, and water, whereby AAHT is produced.

Another novel way of preparing an alkanoyl alkanoate hexamethylene tetraamine comprises the steps of:
(a) combining hexamine with water in a ratio of at least six moles of water per mole of hexamine, thereby forming an aqueous mixture comprising hexamine hexahydrate;
(b) cooling the mixture to at least about −10° C.;
(c) adding to the mixture an alkanoic acid anhydride having the formula (RCO)2O, where R is straight chain or branched alkyl having 1–5 carbon atoms, with the mixture being at a temperature of −10° C. or lower, thereby producing an alkanoyl alkanoate hexamethylene tetraamine.

As indicated above, preferably the alkanoic acid anhydride is acetic anhydride and the alkanoyl alkanoate hexamethylene tetraamine is AAHT. It is also preferred that the aqueous mixture is at or below about −30° C. in step (b), most preferably by addition of ice pre-cooled to a temperature below about −30° C. This process can suitably use about 2.0–2.5 moles of alkanoic acid anhydride per mole of hexamine, most preferably about 2.0–2.2 moles of alkanoic acid anhydride per mole of hexamine. Optionally, the anhydride can be pre-cooled to at least about −30° C. prior to its addition.

One specific embodiment of this second way of making AAHT comprises the steps of:
(a) combining hexamine with water in a ratio of at least six moles of water per mole of hexamine, thereby forming an aqueous mixture;
(b) cooling the mixture to at least about −10° C., thereby forming hexamine hexahydrate; and
(c) adding to the mixture acetic anhydride that has been pre-cooled to at least about −30° C. prior to its addition, whereby the temperature of the mixture is kept at −10° C. or lower, thereby producing AAHT.

A fourth aspect of the invention relates to dialkanoyl, dialkanoate-1,3,5,7-tetraazacyclooctane compounds, wherein the alkanoyl groups each have 2–6 carbon atoms and the alkanoate groups each have 3–8 carbon atoms. For example, such compounds can have the formula

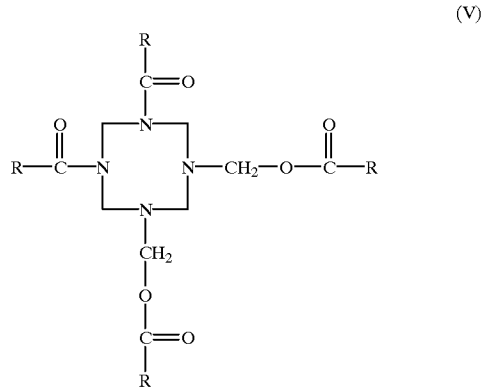

(V)

wherein R is straight chain or branched alkyl having 1–5 carbon atoms. Alternatively, two R groups can be linked as part of a bidentate polymeric moiety. In one preferred compound in this class, R is methyl.

This aspect of the invention also relates to a process for making such a 1,3,5,7-tetraalkanoyl-1,3,5,7-tetraazacyclooctane compound, comprising the steps of.

(a) reacting a compound having the formula

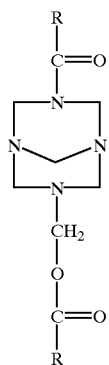
(IV)

wherein R is straight chain or branched alkyl having 1–5 carbon atoms, with an alkanoic acid anhydride having the formula $(RCO)_2O$, where R is straight chain or branched alkyl having 1–5 carbon atoms, at a temperature greater than about 50° C., thereby forming a compound having the formula

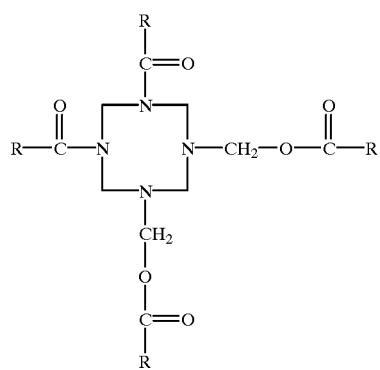
(V)

wherein R is as defined above; and (b) contacting the compound having the formula (V) with water in the presence of a catalytic amount of at least one transition metal oxide, thereby producing a compound having the formula

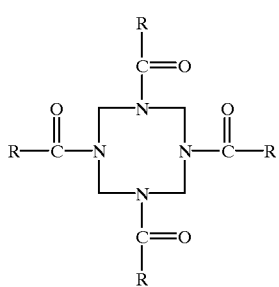
(III)

wherein R is as defined above. As before, preferably the alkanoic acid anhydride is acetic anhydride, and the product of step (b) comprises TAT.

Preferably the reaction of step (a) takes place at a temperature of at least about 100° C., most preferably at about 110–120° C. The presently preferred transition metal oxide catalysts are copper oxides, iron oxides, or mixtures thereof. It is also preferred to use about 24 moles of alkanoic acid anhydride per mole of compound having the formula (IV).

One specific embodiment of this process comprises the steps of: (a) reacting AAHT with acetic anhydride at a temperature greater than about 50° C.; and (b) contacting the product of step (a) with water in the presence of a catalytic amount of at least one transition metal oxide.

Another embodiment comprises the steps of: (a) reacting AAHT with acetic anhydride at a temperature greater than about 100° C., thereby forming the diester derivative of AAHT; and (b) reacting the diester with water in the presence of a catalytic amount of at least one transition metal oxide, thereby producing TAT.

Although one desirable use of this process is to make the diester (i.e., a dialkanoyl, dialkanoate-1,3,5,7-tetraazacyclooctane) for use in making TAT or an analog thereof, it is also possible to stop the process at the point at which the diester has been formed and recover it.

Among the advantages of this process is that the reaction can be carried out at much lower temperatures than those required for making TAT from DAPT. The reduction in temperature increases the yield as well as the safety of the process.

A fifth aspect of the invention is a process for making a 1-(N)-alkanoyl-3,5,7-trinitro-cyclotetramethylenetetramine compound. This process comprises the steps of:

(a) combining a compound having the formula

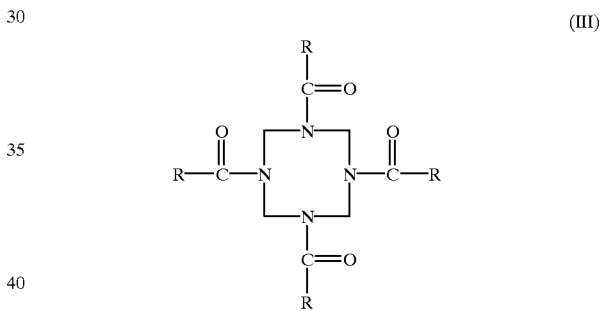
(III)

wherein R is straight chain or branched alkyl having 1–5 carbon atoms, with nitric acid at a temperature between about 15–50° C., thereby producing a reaction mixture; and (b) adding phosphorus pentoxide to the reaction mixture, whereby a compound having the formula

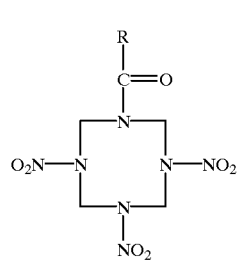
(VI)

is formed, wherein R is as defined above.

As stated above, preferably each R group is methyl, and thus the product is SOLEX. The temperature in step (a) preferably is between about 20–40° C., most preferably about 20–30° C. It is also preferred that the weight ratio of nitric acid to the compound having the formula (III) is between about 0.5:1 to about 5:1, most preferably about 1.5:1. (Preferred weight ratios are given for the embodiment where R is methyl. The preferred weight ratio would change if R was changed.) Preferably the weight ratio of phosphorus pentoxide to the compound having the formula (III) is no greater than about 1:1, more preferably no greater than about 0.75:1, most preferably no greater than about 0.5:1.

The rate of reaction can be controlled by controlling the rate of addition of phosphorus pentoxide to the reaction mixture, or (less desirably) by applying external cooling to the reaction mixture. In either method, control can be in response to measurements of the temperature of the reaction mixture. The extent of the nitration of the compound having the formula (III) can be controlled by using a molar excess of that compound. The extent of the excess of compound (III) limits the extent of the conversion.

One specific embodiment of this process produces SOLEX and comprises the steps of:

(a) combining TAT with nitric acid at a temperature between about 10–15° C., thereby producing a reaction mixture; and (b) adding phosphorus pentoxide to the reaction mixture at a controlled rate, whereby SOLEX is formed.

This process requires much less phosphorus pentoxide than prior methods of making SOLEX. This aspect of the invention takes advantage of the fact that SOLEX is relatively stable, (having twice the impact resistance of RDX), is easily isolated, and can be produced using a far smaller amount of nitrating agent than is required for the direct preparation of HMX from TAT. Further, SOLEX can be readily converted into alpha-HMX, as described below.

Another way of making such a 1-(N)-aalkanoyl-3,5,7-trinitro-cyclotetramethylenetetramine compound comprises the steps of:

(a) combining nitric acid and phosphorus pentoxide, thereby producing a reaction mixture; and (b) adding to the reaction mixture a compound having the formula

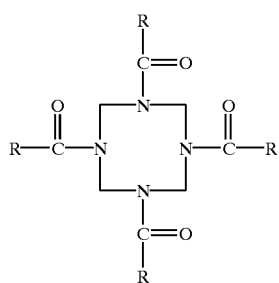

(III)

wherein R is straight chain or branched alkyl having 1–5 carbon atoms; wherein the reaction mixture is kept at temperature no greater than about 68° C.; and whereby a compound having the formula

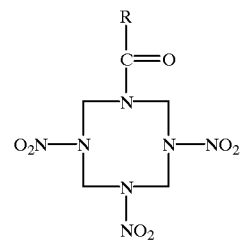

(VI)

is formed, wherein R is as defined above.

In one preferred embodiment of this process, each R group is methyl, and thus the compound having the formula (VI) is SOLEX. Preferably the weight ratio of nitric acid to phosphorus pentoxide in step (a) is from about 2:1 to about 4:1, more preferably about 3:1. The weight ratio of nitric acid to the compound having formula (III) preferably is from about 1.5:1 to about 3.0:1, and the weight ratio of phosphorus pentoxide to the compound having formula (III) preferably is from about 0.5:1 to about 0.75:1.

It is also preferred that the temperature of the reaction mixture in step (a) is about 0–30° C., and that the temperature of the reaction mixture is allowed to rise no higher than about 40–68° C., more preferably no higher than about 45–55° C.

Another embodiment is a process for nitrating TAT comprising the steps of (a) combining TAT and nitric acid to form a reaction mixture having a temperature of about 15–50° C.; and (b) adding $P_2O_5$ to the reaction mixture. The product of step (b) can comprise HMX, SOLEX, or a mixture thereof. The product preferably has a melting point of about 260–281° C., more preferably about 270–281° C. The extent of the nitration, i.e., whether the conversion stops at SOLEX, or produces a mixture of SOLEX and HMX, or pure HMX, can be controlled by using a molar excess of TAT.

A sixth aspect of the invention is a process for making HMX. One embodiment of the invention produces alpha-HMX, and, comprises the steps of:

(a) combining phosphorus pentoxide and nitric acid at a temperature of about 0–25° C., forming a reaction mixture; and (b) adding a compound having the formula

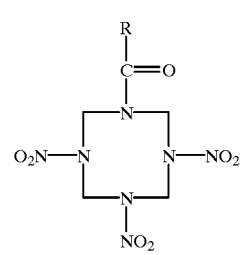

(VI)

wherein R is straight chain or branched alkyl having 1–5 carbon atoms, to the reaction mixture, whereby a product comprising alpha-HMX is produced. This reaction is preferably a solid-state nitration reaction, i.e. the SOLEX reacts while still a solid rather than being dissolved in the nitric acid. In one preferred embodiment of this process, the compound having the formula (VI) is SOLEX.

Preferably the temperature in step (a) is about 10–20° C., most preferably about 15° C. It is also preferred that the nitric acid has a concentration of at least about 98% by weight.

The HMX produced by this process is at least 99% by weight alpha-HMX, often essentially 100% alpha-HMX. Further, the yield of alpha-HMX is typically at least 99%.

One specific embodiment of this process for making alpha-HMX comprises the steps of:
(a) adding phosphorus pentoxide to nitric acid at a temperature of about 0–25° C., forming a reaction mixture; and
(b) adding SOLEX to the reaction mixture, whereby a solid-state nitration reaction produces alpha-HMX.

The invention also relates to the alpha-HMX product made by the above-described process. This product is extremely pure alpha-HMX, e.g., essentially no RDX or beta-HMX contamination. For example, the product can be 99 weight % or more alpha-HMX. In a preferred embodiment, the product comprises less than 0.01% by weight RDX, more preferably no RDX whatsoever. The majority by weight (i.e., greater than 50% by weight) of the alpha-HMX particles produced by this process have the form of long fibers. A majority by weight of these alpha-HMX fibers have an aspect ratio (length:diameter) of at least about 50:1, sometimes as great as at least about 100:1 or even 1,000:1.

The alpha-HMX can be made into long fibers by dissolving the alpha-HMX in boiling aqueous solution (e.g., in pure water), and then cooling the solution below the boiling point. These steps form fibrous alpha-HMX. In one embodiment, the majority by weight of the alpha-HMX produced upon cooling is fibers having an aspect ratio (length:diameter) of at least about 50:1, more preferably at least about 100:1, most preferably at least about 1,000:1. In particular, the product of these steps will typically be a mass comprising a plurality of such fibers. This material can be pressed or otherwise shaped into useful articles.

In one embodiment, the product is an equilibrium mixture, as described above, of alpha-HMX (making up by far the majority of the product) and SOLEX (making up a very small percentage, usually much less than 1% of the product).

Preparing alpha-HMX by the synthetic route that goes through SOLEX helps control the polymorphic form of the product, permitting the manufacture of pure (or very nearly pure) alpha-HMX at essentially quantitative yield.

Another way of making an HMX composition comprises the steps of:
(a) combining a compound having the formula

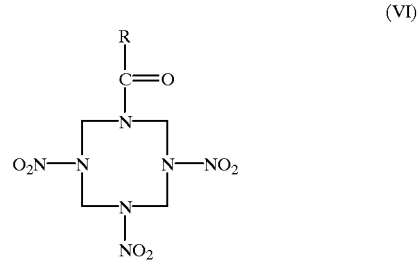

(VI)

wherein R is straight chain or branched alkyl having 1–5 carbon atoms, with nitric acid, thereby forming a reaction mixture; and (b) adding phosphorus pentoxide to the reaction mixture, whereby a product that comprises HMX is produced. The compound (VI) preferably is dissolved in nitric acid and the reaction takes place in solution. The HMX produced in this way can be converted easily to beta-HMX by contacting it with an organic solvent, e.g., heated acetone. This provides a less expensive method of manufacturing beta-HMX than the conventional direct synthesis methods.

In one preferred embodiment of this method, the compound having the formula (VI) is SOLEX. In another embodiment, the product of step (b) comprises an equilibrium mixture of alpha-HMX and SOLEX. The melting point of the product of step (b) preferably is at least about 277° C. (All melting points given herein are as determined by capillary methodology.)

When the R group is methyl (i.e., the group pendant from the N is acetyl) it is preferred that the weight ratio of nitric acid to SOLEX in step (a) is from about 1.5 to about 3.0, more preferably about 1.8. It is also preferred that the weight ratio of phosphorus pentoxide to the compound having the formula (VI) is from about 0.25 to about 2.0, more preferably about 0.7–0.8. The product made by the above-described process comprises HMX. Without being bound by theory, the HMX made by this particular process may be a form of alpha-HMX, or it may be a different polymorphic form of HMX. As long as the product's melting point is at least about 277° C., it can easily be converted to highly pure beta-HMX by contacting the product with a hot organic solvent (e.g., acetone at a temperature of 40–100° C., preferably about 56° C.).

In any of these embodiments of the process, when the nitration reaction has proceeded to the desired extent, the reaction can be stopped by cooling the reaction mixture (e.g., by adding ice). Optionally, a process of making HMX as described above can further comprise the following back-end steps:
(c) filtering the product of step (b), whereby alpha-HMX is retained by a filter and an impurity-containing filtrate is collected;
(d) treating the filtrate with a source of ammonium ions to adjust its pH to about 4.0–5.0;
(e) evaporating water from the filtrate; and
(f) cooling the filtrate sufficiently to crystallize ammonium nitrate crystals.

These additional steps produce a highly pure ammonium nitrate byproduct, which can be sold for use in fertilizer or the like. Thus, these additional steps enhance the economics of the process by reducing the amount of waste material that must be disposed of and creating a valuable byproduct. In these steps, preferably the pH of the filtrate is adjusted to about 4.7 and the source of ammonium ions is ammonia.

Alternatively, instead of performing steps (c)–(f) after filtration to remove the solid product, the remaining nitric acid can be concentrated for recycle.

A seventh aspect of the invention relates to compositions and articles that comprise HMX, as well as processes for making them.

One such composition comprises HMX particles (e.g., alpha-HMX particles) and at least one second material coated thereon and/or sorbed into voids in the particles. The term "second material" is used herein to refer generically to materials other than alpha-HMX which can be combined with alpha-HMX to form mixtures, granules, and/or shaped articles. Preferably, a majority by weight of the alpha-HMX particles are in the form of fibers, which may be porous (i.e., contain some void spaces). Typically a majority by weight of the alpha-HMX fibers have an aspect ratio (length:diameter) of at least about 50:1, often as great as about 1,000:1 or even higher.

A variety of second materials can be used in the invention, including mixtures of two, three, or more different second materials. One suitable example of a second material is an energetic material, such as beta-HMX, RDX, TNT, ammonium nitrate, or a mixture thereof. Another suitable example of a second material is a fuel, such as aluminum, lithium hydride, lithium aluminum hydride, or a mixture thereof. As another example, a first set of particles can have coated and/or sorbed thereon one component of a binary explosive, and a second set of particles can have coated and/or sorbed thereon the other component of the binary explosive (e.g., material comprising nitro moieties and glycerin). When the two sets of particles are combined, a binary explosive composition can be formed.

Yet another suitable example of a second material is one that alters the structural properties of the composition as compared to the structural properties of the alpha-HMX particles in the absence of the second material. For instance, the second material can be one that increases the durability, density, or structural strength of the composition, such as carbon fibers or silicone molding resins. Another suitable example of a second material is one or more polymerizable monomers, such as caprolactam, or a mixture of adipic acid and hexamethylene diamine. It is possible to polymerize such monomers in situ after they are coated onto the alpha-HMX, thereby providing additional strength or other desirable properties. By coating a HMX particle with such monomers, forming a plurality of such articles into a granule or article, and then polymerizing the monomers in situ, an HMX-containing granule or article can be formed that also comprises a polymeric "cage" or framework.

It is also possible to use multiple layers of coatings comprising second materials. For instance, the composition can comprise a plurality of layers coated on the alpha-HMX particles, each layer comprising at least one second material. The second material can be the same in each of the plurality of coated layers. Alternatively, at least two of the plurality of coated layers comprise different second materials, or each coated layer can comprise a different second material.

This aspect of the invention also relates to durable alpha-HMX containing articles, comprising a plurality of particles, the particles comprising alpha-HMX coated with at least one second material. A "durable article" in this context is one that will retain is shape under normal handling.

In such an article, the plurality of coated alpha-HMX particles can optionally comprise (a) a first group of alpha-HMX particles coated with a second material, and (b) a second group of alpha-HMX particles coated with a different second material. For example, the different second materials could be ones that can be combined to firm a binary explosive. Then when the two groups (a) and (b) are combined, the overall composition is explosive.

The article can suitably be formed by pressing the plurality of coated particles into a shape, or by granulating a plurality of such particles, using techniques described below. The article can further comprise a coating of a second material on the exterior of the article, or even a plurality of coatings of one or more second materials on its exterior. As outlined above, the second material can be the same in each of the plurality of coatings, can be different in at least two of the coatings, or can be different in each coating.

In one particular embodiment, the article further comprises a coating on the exterior of the article. This coating comprises alpha-HMX particles that have been coated with a second material. Alternatively, the article can comprise a plurality of coatings, each of which comprises alpha-HMX particles that have been coated with a second material.

The article can also comprise a second material that has been sorbed into the article, or onto an alpha-HMX particle. A process for sorbing a second material onto alpha-H particles, comprises the steps of:

(a) providing at least one second material;

(b) mixing the second material with a liquid solvent;

(c) contacting the solvent with alpha-HMX particles; and (d) evaporating the solvent, whereby the second material sorbs onto and/or into the alpha-HMX particles.

The second material can initially be in a variety of forms (e.g., solid particulates, liquid, or gas).

In one embodiment, the solvent of step (b) is an organic solvent, such as acetone, cyclohexane, gamma butyrolactone, or a mixture of one or more of these. This process can further comprise the step of forming a granule that itself comprises a plurality of the alpha-HMX particles having the second material coated on the particles. The granules and articles formed as described above are highly stable, for example holding their structural integrity in boiling water or acetone.

The combination of materials involved in this aspect of the invention can achieve a higher level of energy per unit volume, thus making the composition highly desirable for use as an explosive or propellant. Depending on what secondary materials are used, the composition can also have its energetic properties per unit volume increased, or its structural strength, density, or durability increased. These enhancements are especially useful for making various explosive, propellant, and pyrophoric devices (e.g., shaped charges).

An eighth aspect of the invention is a process for making beta-HMX. This can be accomplished by a process that comprises the steps of:

(a) combining a compound having the formula

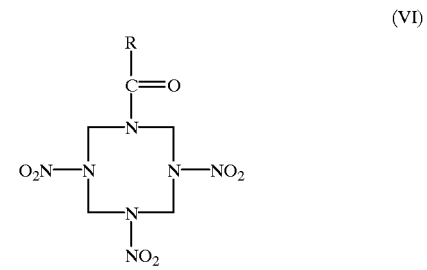

(VI)

wherein R is straight chain or branched alkyl having 1–5 carbon atoms, with nitric acid, thereby forming a reaction mixture;

(b) adding phosphorus pentoxide to the reaction mixture, whereby a product that comprises HMX is produced;

(c) contacting the so-produced HMX with a solvent; and (d) evaporating the solvent, whereby beta-HMX crystals are formed.

This aspect of the invention allows the manufacture of beta-HMX by conversion of a different form of HMX (e.g., alpha-HMX). The HMX used as the starting material preferably is made by a process comprising the steps of:

(a) combining a compound having the formula

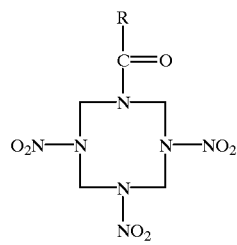

(VI)

wherein R is straight chain or branched alkyl having 1–5 carbon atoms, with nitric acid, thereby forming a reaction mixture; and (b) adding phosphorus pentoxide to the reaction mixture, whereby a product that comprises HMX is produced. The compound (VI) preferably is dissolved in nitric acid and the reaction takes place in solution. The melting point of the product of step (b) preferably is at least about 277° C.

The conversion process comprises the steps of:
(a) contacting the so-produced HMX with a solvent;
(b) evaporating the solvent, whereby beta-HMX crystals are formed.

In one embodiment, the HMX is dissolved or suspended in the solvent in step (a). In a specific embodiment of the process, the solvent is an organic solvent, such as acetone, cyclohexane, gamma butyrolactone, or a mixture of one or more of these.

Optionally, seed crystals of beta-HMX can be added to the solvent to facilitate crystallization. However, seed crystals are generally not required. If seed crystals are used, they can be provided, for example, by including no more than about 1% by weight (preferably no more than about 0.1%) beta-HMX in the HMX of step (a). If a small amount of beta-H byproduct is present in the starting HMX composition, it can serve this purpose. Alternatively, the beta-HMX crystals can provided by adding them to the solvent from an external source.

In one preferred embodiment of the process, the solvent is evaporated by spray drying. This spray drying can suitably take place at a temperature of less than about 56° C., preferably at about 50° C. This process can produced Class 5 beta-HMX, or even finer particles.

A ninth aspect of the invention is a process for forming alpha-HMX containing granules from at least one particulate material, comprising the steps of:

(a) selecting particulates having a particle size distribution; and
(b) fluidizing the particulates, whereby particulates agglomerate to form granules.

In one embodiment, this process involves accelerating the fluidized particulates against a solid surface, and more preferably, continuously impacting such particulates against a surface, most preferably a curved surface. Vessels having circular cross-sections are well suited for performing this operation. A rotating impeller, or alternatively a gas stream, can suitably be used to accelerate the particles.

Although this process is especially well-suited for producing granules from alpha-HMX particles made as described above, it is not limited to use with that particular material. This process can be used with a variety of particulate materials, such as drugs and pharmaceutical excipients.

In one preferred embodiment, the fluidized particulates are impacted against a solid surface, for example by being circulated around a circular or elliptical path. Preferably, the particulates are circulated in a channel in a vessel, whereby the motion creates centrifugal force that impacts the particulates against the solid surface of the channel, whereby a granule is formed that tumbles as it continues to circulate around the channel.

The particle size distribution in step (a) can be any desired range, including taking particulate alpha-HMX and using it as-is. Alternatively, a particle size distribution can be cut from the initial material, for example by sieving.

Optionally, a small amount of an organic solvent (e.g., about 0.001–0.5 g of organic solvent per g of alpha-HMX or other particulate material, more preferably about 0.05–0.1 g of solvent per g of particulates) can be added to the particulates. This small amount of solvent helps fluidize the particles, and facilitates formation of a granule, but does not dissolve a large percentage of the alpha-HMX, which could cause the eventual formation of a different polymorph.

Fluidization of the particles can be achieved, for example, by placing them in high velocity gas streams (e.g., "sand-blasting"). The density of the resulting granules can be controlled by selecting the amount of kinetic energy imparted to the particles in step (b). In other words, the greater the velocity of the gas steam(s) in which the particles are fluidized, the denser the resulting granules will be.

Optionally, the alpha-HMX particulates can be coated and/or impregnated with one or more second materials, as described above, such as energetic materials or fuels. If one or more of the second materials comprise polymerizable monomers, the process can optionally further comprise the step of polymerizing those monomers in situ, either before or after the granule is formed.

In one particular embodiment, a second material is sorbed onto the alpha-HMX particles by a process comprising the steps of:

(a) providing at least one second material;
(b) mixing the second material with a liquid solvent;
(c) contacting the solvent with alpha-HMX particles; and
(d) evaporating the solvent, whereby the second material adsorbs onto the alpha-HMX particles.

This aspect of the invention also relates to a durable article that consists essentially of alpha-HMX and at least one second material. In other words, this article need not comprise any binder; the properties of the alpha-HMX particles allow them to be formed into a durable article in a mixture with the second material, without requiring the inclusion of a material with adhesive properties. Optionally, such an article can comprise no more than about 2% by weight graphite, to facilitate manufacturing the article.

The second materials included in such an article can be varied, as described above. One particularly useful second material in this aspect of the invention is aluminum in particulate form. One particular embodiment of the invention is an article as described above that comprises about 0.1–20% by weight aluminum. One especially useful embodiment is a durable article that consists of alpha-HMX and about 0.1–20% by weight aluminum.

This aspect of the invention also relates to a process for making an alpha-HMX composition, comprising the steps of:

(a) mixing particulate alpha-HMX and at least one particulate material selected from the group consisting of energetic materials and fuels, thereby forming a particulate mixture;
(b) fluidizing the particulate mixture; and
(c) impacting the particulate mixture against a solid surface, whereby the particulates in the mixture agglomerate to form granules.

As mentioned above, the particulate mixture can be circulated around a circular or elliptical path, for example in a channel in a rotating vessel.

The granules formed from alpha-HMX particles will typically contain void spaces. Therefore, the process can optionally further comprise the step of sorbing a second material into the granules. This can be done by using a vacuum to a gas phase that comprises draw the second material into the granule. Alternatively, this can be done by:

(d) mixing the second material with a liquid solvent (e.g., an organic solvent);

(e) contacting the solvent with the granules; and (f) evaporating the solvent, whereby the second material is sorbed into the granules.

These granules will retain their solid, durable character, even with large amounts of secondary materials added, for example even if they contain as much as 90% by weight TNT, and even at temperatures greater than 200° C. Further, the granules are pressable, for example to make explosive devices (e.g., shaped charges). In addition, the composition does not tend to build up static electrical charges. Typically, the granules into whose void spaces a second material has been sorbed will have greater bulk density than the granule in the absence of the sorbed second material.

A tenth aspect of the invention is a process for preparing an HMX product, comprising the steps of:

(a) providing a granule that comprises a plurality of alpha-HMX particles and which has internal void spaces; and (b) sorbing at least one second material into the void spaces in the granule.

The term "HMX product" is used herein to refer generically to compositions that comprise HMX and one or more second materials that have been coated onto and/or sorbed into an alpha-HMX particle, granule, or article. ("Granule" as used herein generally refers to an object that comprises a plurality of particles, while "article" refers to a relatively large object formed into a desired shape that is large enough to be easily visible to the naked eye).

The second material can be sorbed into the granules by using a vacuum to draw a gas phase comprising the second material into the granule. Alternatively, the second material can be sorbed into the granules by:

(c) mixing the second material with a liquid solvent (e.g., an organic solvent);

(d) contacting the solvent with the granules; and (e) evaporating the solvent, whereby the second material is sorbed into the granules.

Various second materials can be used, as explained above. Suitable examples include energetic materials and fuels.

The process can optionally further comprise coating the exterior of the granule with a second material. This second material coated on the exterior of the granule can be the same as the second material sorbed into the granule, or it can be different. As another option, a plurality of coatings can be applied to the exterior of the granule. As yet another option, a mixture of at least two second materials can be sorbed into the granule.

This aspect of the invention also relates to a process for preparing an HMX product, comprising the steps of:

(a) contacting alpha-HMX granules having void spaces therein with an solvent in an amount from about 0.1–2.5 g of solvent per g of alpha-HMX, whereby a fraction of the HMX is dissolved;

(b) providing beta-HMX crystals in the dissolved HMX; and (c) evaporating the solvent, whereby beta-HMX is deposited in void spaces of undissolved alpha-HMX particles.

The solvent can suitably be an organic solvent, for example selected from the group consisting of acetone, cyclohexane, gamma butyrolactone, and mixtures thereof. The beta-HMX crystals can be provided as part of the alpha-HMX granules. If the goal is to fill void spaces in the alpha-HM granules with beta-HMX, then preferably the beta-HMX crystals comprise less than 1% by weight of the alpha-HMX granules, more preferably less than 0.1%. Alternatively, the beta-HMX crystals can be providing by adding them to the solvent from an external source. Either way, it is preferred that the amount of beta-HMX crystals provided in step (b) is no greater than about 1.0% by weight of the alpha-HMX, more preferably no greater than about 0.1% by weight of the alpha-HMX.

Alternatively, if the goal is to produce a granule or article comprising primarily beta-HMX, then the weight ratio of beta to alpha-HMX can be as high as desired (e.g., 1:1 or higher). The relatively small amount of alpha-HMX in this embodiment can serve to bind the beta-H particles together as a granule or article.

The amount of solvent used should be small enough so that only a minor portion of the alpha-HMX is dissolved. Preferably about 10-20 % by weight of the alpha-HMX is dissolved in step (a).

The process can further comprise the step of pressing the product of step (c) into a shaped article.

The product produced by this aspect of the invention has greater bulk density than the original granules or article, due to the incorporation of a second material into the void spaces. If the second material is an energetic material or a fuel, this enhances the overall energetic effect of the article or granule.

An eleventh aspect of the invention is a method of performing an exothermic chemical reaction, comprising the steps of:

(a) contacting reactants to form a liquid reaction mixture in an open reaction vessel, wherein:

(i) the reaction vessel has a closed bottom with a first diameter;

(ii) the reaction vessel has an open top with a second diameter that is greater than the first diameter;

(iii) the reaction vessel has a wall that is connected to the bottom, the wall having an inner surface, at least a part of which contacts the reaction mixture; and (iv) the reaction vessel comprises an adjustable stirrer in contact with the reaction mixture; and (b) controlling the temperature of the reaction mixture by adjusting the degree of stirring of the reaction mixture by the adjustable stirrer, whereby the centrifugal force from the stirring causes the liquid reaction mixture to move upward along the inner surface of the reaction vessel. By placing the reaction mixture in physical contact with a greater surface area of the inner surface of the reaction vessel, cooling of the reaction mixture can be enhanced.

In one embodiment, the reaction vessel is frustoconical in shape. One embodiment of the adjustable stirrer comprises a rotatable impeller which is mounted on a shaft. The shaft is driven by a motor, and thus can rotate the impeller about a vertical axis of the reaction vessel. The method can further comprise applying external cooling to the reaction vessel (for example, with an external jacket through which a heat transfer fluid flows). If the temperature of the reaction mixture exceeds a target temperature, the speed of rotation of the impeller can be increased. This increase in rotational speed will increase the centrifugal force that tends to move the reaction mixture up the walls of the vessel. By placing the reaction mixture in physical contact with a greater surface area inside the vessel, the rate of cooling is increased, and the temperature of the reaction mixture can be decreased.

In the same way, if the temperature of the reaction mixture exceeds a predetermined alarm level, the speed of rotation of the impeller can be increased sufficiently to cause a predetermined amount of the reaction mixture to be expelled from the reaction vessel through its open top, thereby bringing the remaining reaction mixture under thermal control and preventing catastrophic damage to the equipment from excessive reaction temperatures.

Although this method has wide applicability in exothermic reactions, it is particularly useful in one or more of the above-described processes in which a nitramine or nitramine intermediate is manufactured. For example, this method is useful where the reactants comprise hexamine and acetic anhydride; DAPT and acetic anhydride; TAT, nitric acid, and either or both of phosphorus pentoxide or dinitrogen pentoxide; hexamine hexahydrate and acetic anhydride; AAHT and acetic anhydride; or SOLEX, nitric acid, and either or both of phosphorus pentoxide or dinitrogen pentoxide.

One specific embodiment of the invention is a method of performing an exothermic chemical reaction, comprising the steps of:
 (a) contacting reactants to form a liquid reaction mixture in a fiustoconical reaction vessel, wherein:
  (i) the frustoconical reaction vessel has a closed bottom with a first diameter;
  (ii) the frustoconical reaction vessel has an open top with a second diameter that is greater than the first diameter;
  (iii) the frustoconical reaction vessel has a wall that is connected to the bottom the wall having an inner surface, at least a part of which contacts the reaction mixture; and
  (iv) the frustoconical reaction vessel comprising a motor-driven impeller which is rotatable about a vertical axis of the reaction vessel;
 (b) mixing the reaction mixture in the frustoconical reaction vessel by rotating the impeller; and
 (c) controlling the temperature of the reaction mixture by (1) applying external cooling to the frustoconical reaction vessel and (2) adjusting the speed of rotation of the impeller, whereby the centrifugal force from rotation of the impeller causes the liquid reaction mixture to move upward along the inner surface of the frustoconical reaction vessel; wherein when the temperature of the reaction mixture exceeds a target temperature, the speed of rotation of the impeller is increased; and wherein when the temperature of the reaction mixture exceeds a predetermined level, the speed of rotation of the impeller is increased sufficiently to cause a predetermined amount of the reaction mixture to be expelled from the frustoconical reaction vessel through its open top.

This aspect of the invention also relates to chemical reaction apparatus that comprises:
 (a) an open reaction vessel comprising:
  (i) a closed bottom having a first diameter;
  (ii) an open top having a second diameter that is greater than the first diameter;
  (iii) a wall that is connected to the bottom, the wall having an inner surface; and an outer surface; and (b) an adjustable stirrer located within the vessel;
 (c) a temperature sensor within the vessel; and
 (d) a motor that is operationally connected to the adjustable stirrer, the motor being adjustable so as to change the rate of stirring in response to the temperature measure by the temperature sensor.

In one embodiment, the adjustable stirrer comprises an impeller mounted on a rotatable shaft, the impeller being located within the vessel and the shaft extending from the impeller to the motor. The apparatus can further comprise a computer which adjusts the speed of the motor in response to the temperature measure by the temperature sensor.

This aspect of the invention provides an inexpensive, simple, and safe means for performing exothermic reactions, such as those involved in producing alpha-HM and its various intermediates.

A twelfth aspect of the invention is a process for separating a nitramine or nitramine intermediate (e.g., DAPT) from water and volatile organic compounds, comprising the steps of:
 (a) feeding a liquid stream comprising a liquid nitramine or nitramine intermediate (e.g., DAPT), water, and at least one volatile organic compound, into the upper half of a stripper column;
 (b) feeding a gas stream having a temperature of at least about 120° C. into the lower half of the stripper column, whereby the gas stream and the liquid stream come into countercurrent contact in the stripper column;
 (c) withdrawing a nitramine or nitramine intermediate stream from the bottom of the stripper column; and
 (d) withdrawing a waste stream comprising gas and one or more of water vapor, water, formaldehyde, and acetic acid, from the top of the column.

The temperature of the gas stream can suitably be about 70–200° C. In other embodiments of the process, the temperature of the gas stream is greater than about 150° C., or even greater than about 200° C., and no substantial degradation of the nitramine or intermediate occurs, due to the relatively short residence time of the compound in the column.

The gas stream preferably consists essentially of air (optionally comprising some water vapor). It is also preferred that the stripper column comprises packing. The column can optionally be operated at below-atmospheric pressure, which would also change the temperature of operation.

This process is especially useful in the purification of a liquid stream that comprises DAPT. Conventional filtration of such a stream is a relatively slow operation. Therefore, one particularly preferred embodiment is a process for separating DAPT from water and volatile organic compounds, comprising the steps of:
 (a) feeding a liquid stream comprising DAPT, water, and at least one volatile organic compound, into the upper half of a stripper column;
 (b) feeding an air stream having a temperature of at least about 120° C. into the lower half of the stripper column, whereby the gas stream and the liquid stream come into countercurrent contact in the stripper column;
 (c) withdrawing a DAPT stream from the bottom of the stripper column; and
 (d) withdrawing a waste stream comprising air, water vapor, formaldehyde, and acetic acid, from the top of the column.

Preferably the DAPT stream in step (c) comprises no more than about 5% water by weight.

The various aspects of the present invention have numerous advantages over the prior art. One of the most significant advantages is considerably lower cost than prior art methods for making alpha-HMX, in part due to the use of lower temperatures and less reactants. In particular, the synthetic routes of the present invention make possible a five-fold reduction in the cost of manufacturing HMX. The alpha-HMX produced by the methods of the present invention is exceptionally pure, which enhances its performance as an explosive or rocket propellant. Another advantage of the present invention is the ease of manipulation of the final product to modify its properties, for example by combination with other materials, or by pressing into shaped articles, such as shaped charges.

DETAILED DESCRIPTION OF SPECIFIC EMBODIMENTS

Figure 1:
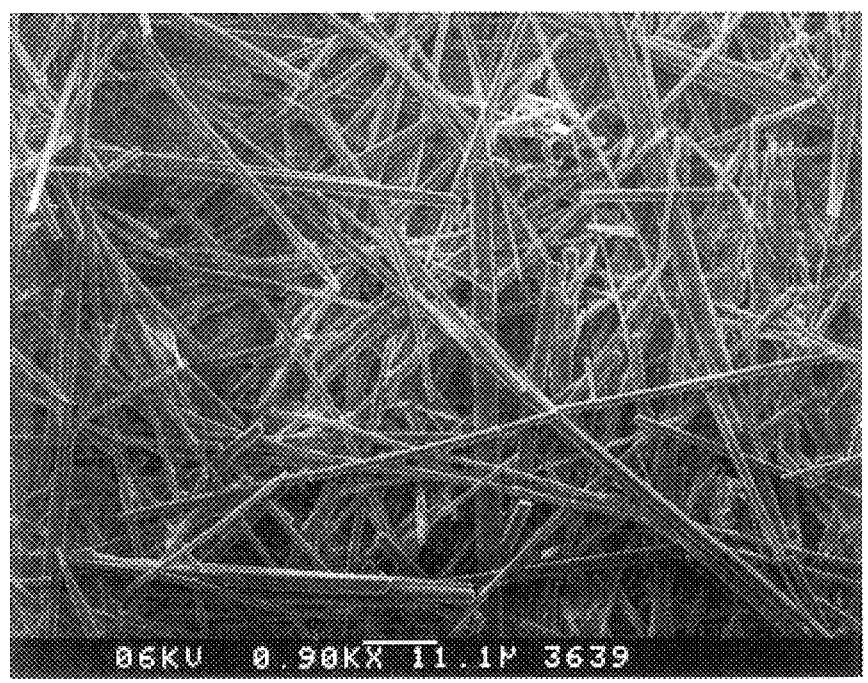
FIG. 1 is a photomicrograph of alpha-HMX particles produced by a process in accordance with the present invention. The white bar at the bottom of the photograph represents a length of 11.1 microns.

The present invention relates to HMX and methods for making it, including some novel intermediates. In addition, the invention also relates to HMX compositions which may comprise other explosive or non-explosive materials.

One synthetic scheme for preparing HMX involves production of the intermediates DAPT and TAT, as described in steps 1A, 1B, and 1C below.

Step 1A: Preparation of DAPT

Rather than dissolving hexamine in acetic acid, the hexamine is first dissolved in room temperature (e.g., 22° C.) water (preferably 1 g water per g hexamine), followed by addition of ice or a mixture of ice and water (preferably 0.5 g per g hexamine). The resulting slurry is then allowed to come to 0C, followed by rapid addition of acetic anhydride (2 moles per mole hexamine). The resulting reaction is extremely rapid (about 1 minute in duration) and is evidenced by the melting of the ice.

One method of isolating the DAPT product can be accomplished in two stages. The first stage involves evaporation of the volatile components. Special care must be taken, however, to avoid the thermal instability of DAPT when it is in the form of, for example, its diacetate salt. Therefore, the solution is heated to 40–45° C. to prevent cooling of the solution caused by evaporation. A stream of flowing air is then passed over the solution. To evaporate the acetic acid selectively, the air is substantially saturated with water vapor (e.g., at least 95% saturated), allowing the acetic acid to be preferentially evaporated. The formaldehyde produced by the conversion of hexamine to DAPT is removed during the evaporation of the water. Some polymerization of the formaldehyde occurs, resulting in an insoluble precipitate. The evaporation is continued until the DAPT acetate salt begins to precipitate.

The second stage of purification involves the removal of the polymeric formaldehyde, as well as any remaining water and acetic acid. When approximately ⅔ of the solution has been evaporated (at which point the byproduct DAPT acetate salt has begun to precipitate), the reaction mixture is brought to 130–140° C. for a period ranging from 20–30 minutes. The temperature must be raised above about 130° C. in order to promote depolymerization of the formaldehyde, as well as driving off any remaining water or acetic acid. However, the temperature must not be allowed to rise above approximately 150° C., because DAPT will start to decompose at this temperature. The DAPT is then removed from the heat and air jet, and the system is cooled.

However, if the DAPT product is to be used in a subsequent reaction in which it is converted to TAT, and that subsequent reaction uses one or more transition metal oxides as a catalyst, then the temperature of the reaction mixture can be as low as about 70° C. in the second stage of purification. This is because the transition metal oxide will catalyze the depolymerization of formaldehyde polymers during the subsequent conversion to TAT. Therefore, in that situation, the temperature of the reaction mixture need not be increased to 130° C. or higher, because depolymerization of the formaldehyde polymers is not necessary at that point.

Yet another way of isolating DAPT and removing volatile materials involves the use of a stripper column. In general, in this embodiment of the process, the raw DAPT-containing product stream is fed to the upper half of a stripper column. A stream of hot gas (e.g., air at about 120° C. or greater) is fed to the lower part of the column, so that the rising gas and the descending liquid come into countercurrent contact. Volatile materials in the liquid are vaporized and carried out of the stripper along with the gas stream. Apparatus suitable for use in this purification technique is described in more detail below.

Without being bound by theory, it is believed than the relatively short time of contact between the DAPT and the hot gas in the stripper column helps avoid thermal degradation of the DAPT, and this permits the use of gas at temperatures even greater than 120° C. In particular, the relative concentration of acetic acid decreases as it moves down the column, and the DAPT tends to convert from salt to free base. Since DAPT as free base has greater thermal stability than its salts, contact with the hottest gas near the bottom of the column will not cause substantial degradation of the DAPT.

By the above-described synthesis process, nearly quantitative yields of DAPT are obtained in a matter of minutes. The need to use excess reactant (acetic anhydride) to push forward equilibrium has been substantially diminished. The stoichiometry of the reaction requires 2 moles of acetic anhydride per mole of tetraamine. A slight excess (e.g., 2.1 to 2.5 moles) of acetic anhydride can be used, if desired, but an essentially stoichiometric amount is generally sufficient and therefore preferred.

The ice advantageously functions as a heat sink for the reaction exotherm. This enhances the product yield and shortens the reaction time. The ice can be provided in any convenient form (e.g., cubes, chips, shaved ice, or slivers) but crushed ice is preferred because of its high surface area and ready availability.

The reaction can be conducted in any appropriate reactor that provides efficient stirring, including reactors that are jacketed and equipped with external cooling apparatus. The reaction yields are optimized by maintaining the reactant mixture at a low temperature. The reaction temperature is usually maintained between about −30° C. and 10° C., and is preferably maintained between about −15° C. and 0° C., most preferably at 0° C. (i.e., ice water conditions). Advantageously, the acetic anhydride is added to a pre-cooled (e.g., pre-cooled to at least about −10° C., more preferably to at least about −30° C.), stirred mixture of (a) tetraanine and (b) ice water.

Step 1B: Conversion of DAPT to TAT

The synthesis of TAT is accomplished by first converting DAPT into an ester (see reaction 1 below), hydrolyzing the ester, and then reacting with acetic anhydride (reaction 2). The ester can also be isolated or used as it is formed.

About 2.0–2.5 moles of acetic anhydride are used in reaction 1 per mole of DAPT. Preferably the temperature is kept below the reflux temperature (1388C) initially, and after the initial exotherm, preferably the temperature is kept at 110–120° C. until conversion of DAPT to the ester is complete.

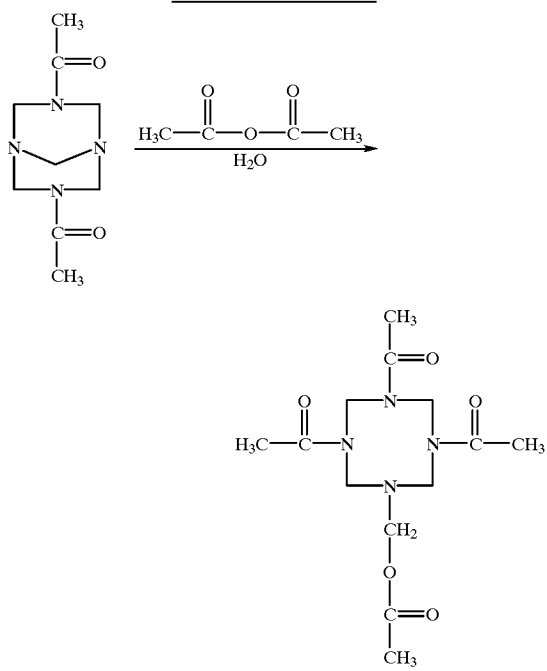

Reaction 1: DAPT to ester

The reactive ester is converted to TAT in the presence of water and a transition metal oxide catalyst, such as a mixture of copper oxide and iron oxide. Under these conditions, the reactive ester undergoes hydrolysis, resulting in the formation of a primary alcohol. The primary alcohol is unstable in this environment, and it quickly decomposes, producing formaldehyde and a secondary amine. The secondary amine then reacts with a second mole of acetic anhydride, giving the desired TAT product. Reaction 2 shows this process.

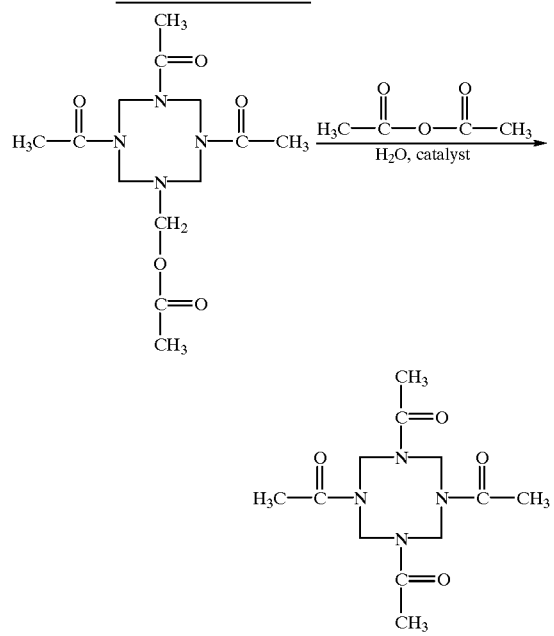

Reaction 2: Ester to TAT

Step 1C: Conversion of TAT to HMX

TAT can be converted to alpha-HMX by reaction with 98+% nitric acid and either phosphorus pentoxide or dinitrogen pentoxide, at a temperature between room temperature and about 40° C. Suitable procedures are disclosed in Lukasavage U.S. Pat. Nos. 5,124,493 and 5,268,469, both of which are incorporated herein by reference. Alternatively, TAT can be converted to HMX as described below in steps 2C–2D, or 2E–2F.

A second synthetic scheme for producing HMX has also been invented. This process involves the use of a novel intermediate, acetyl acetate hexamethylene tetraamine (which is referred to herein as AAHT), that contains both an acetate group and an acetyl group. Unlike the synthetic route to HMX that goes through DAPT, the acetate intermediate (AAHT) does not undergo hydrolysis (which would produce formaldehyde and a second acetyl group), but instead can be isolated. This novel intermediate has the advantages of being more stable than DAPT and being easier to convert into TAT.

AAHT has the chemical formula shown below, with R being methyl.

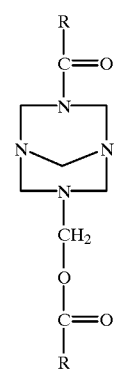

This second synthetic scheme is described in steps 2A, 2B, 2C, and 2D below.

Step 2A: Preparation of AAHT

Two processes have been developed for making AAHT. The first process comprises reacting a hexamine/ice/water slurry with acetic anhydride at temperatures between −78° C. (which can be achieved, for example, by using a dry ice/acetone bath) and −0° C., most preferably at about −30° C. Approximately 2 moles of acetic anhydride are added to the slurry per mole of hexamine. The product of this reaction is AAHT. The reaction preferably is conducted in a stainless steel or aluminum vessel equipped with an efficient stirrer.

This method can be applied to synthesize any common derivative of AAHT, simply by varying the anhydride used; the reaction scheme described above is not limited to acetic anhydride. This general scheme is shown in reaction 3.

Reaction 3: Hexamine to AAHT

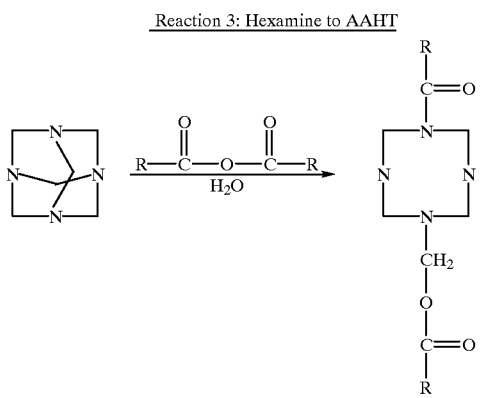

Optionally the ice can be pre-cooled to a temperature of −30° C. or lower, which will allow the use of less ice in the reaction.

The second method for making AAHT comprises reacting hexamine hexahydrate with approximately 2 mole equivalents of acetic anhydride at temperatures between −78 and −0° C., most preferably at about −30° C. AAHT is obtained as a waxy solid material.

Step 2B: Conversion of AAHT to TAT

TAT can be produced from AAHT by first forming the diester derivative of AAHT. The diester has the general formula shown below.

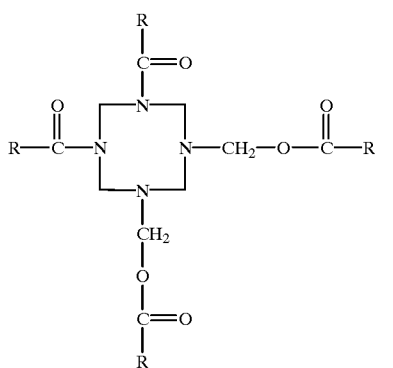

To form the diester, about 2–4 moles of acetic anhydride are added per mole of AAHT. This reaction mixture is then heated (e.g., to 110–120° C.) and stirred for a time sufficient to complete synthesis of the diester. Volatile components in the product mixture can be removed by evaporation, allowing isolation of the diester.

Alternatively, instead of recovering the diester, it can be converted to TAT in situ. The reaction mixture containing the diester is allowed to cool to a temperature between about 0–50° C., preferably to room temperature (about 22° C.), and transition metal oxide catalysts are added, preferably iron and copper oxides. The formaldehyde generated during the course of the hydrolysis should be allowed to escape from the reaction mixture. About 2–4 moles water per mole of diester are then gradually added (e.g., over a period of about 90 minutes), at which point the hydrolysis is complete. TAT is purified by heating to greater than 100° C. under an air jet, which evaporates the acetic acid byproduct and any water that is coordinated to the TAT.

The conversion of AAHT to diester and then to TAT is shown in reaction 4.

Reaction 4: Conversion of AAHT to TAT

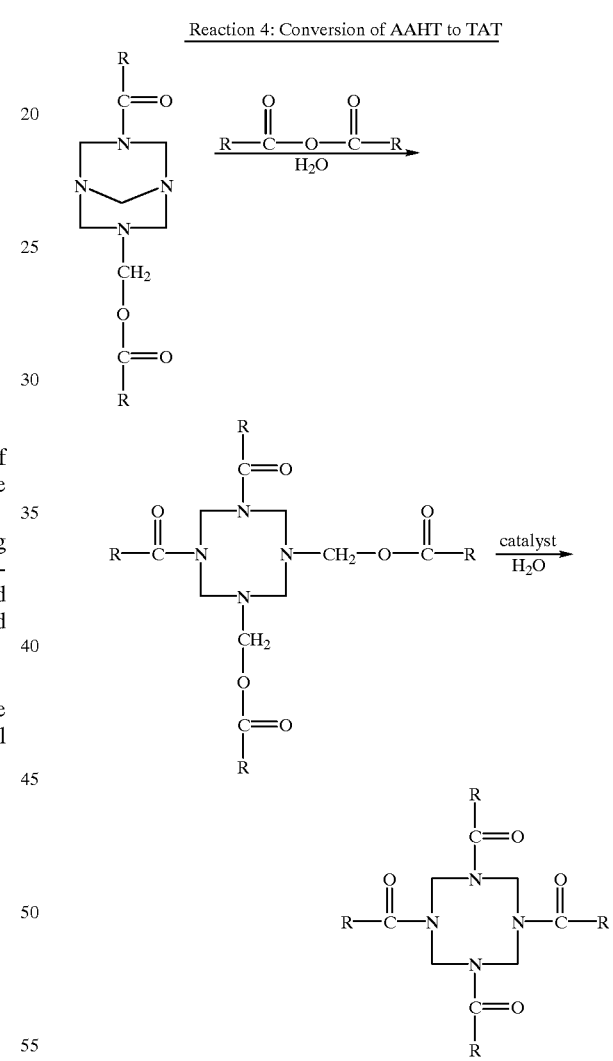

Step 2C: Conversion of TAT to SOLEX

An improved process has been discovered for preparing SOLEX (1-(N)-acetyl-3,5,7-trinitro-cyclotetramethylenetetramine) from TAT. By lowering the temperature of the reaction mixture and by changing the order of addition of the reagents used in prior methods, the amount of nitrating agent required can be reduced significantly.

The preparation involves mixing TAT and low concentrations of nitrating agents, namely phosphorus pentoxide and nitric acid. (It should be understood that the TAT can be prepared, for example, by the procedure of step 1B or step 2B.)

TAT is added to nitric acid in a reactor. The nitric acid preferably is at a temperature between about 0° C. and 25° C., most preferably 10–15° C. The weight ratio of nitric acid to TAT preferably is at least about 0.5:1, most preferably about 1.5:1. To this reactant mixture of nitric acid and TAT, phosphorus pentoxide is added slowly with stirring over a period of several hours. The reaction is strongly exothermic and the reaction temperature should be carefully monitored, and controlled if necessary, by slowing the addition of phosphorus pentoxide to the reactant mixture and/or by external cooling to prevent a potentially dangerous exotherm from occurring. The reaction is normally complete within a few hours (e.g. 3 hours). SOLEX is produced in essentially quantitative yields and high purity.

This method for preparing SOLEX is shown in reaction 5 (R is methyl in this instance).

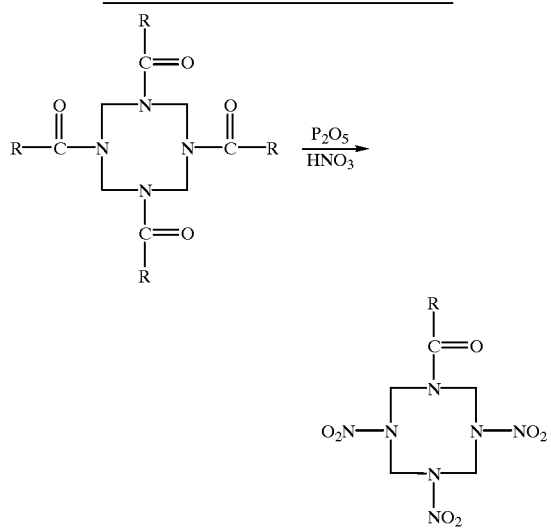

Another way of making SOLEX involves combining nitric acid and phosphorus pentoxide, preferably at a temperature of about 0–30° C., then adding TAT to the reaction mixture. Preferably after the addition of TAT, the reaction mixture is kept at temperature no greater than about 68° C., more preferably no higher than about 45–55° C. Preferably the weight ratio of nitric acid to phosphorus pentoxide is between about 2:1 to about 4:1, more preferably about 3:1. The weight ratio of nitric acid to TAT preferably is at least about 1.875:1.

Step 2D: Conversion of SOLEX to alpha-HMX

A novel method for converting SOLEX to alpha-HMX involves a solid-state nitration reaction. That is, the SOLEX reactant is not dissolved in a reaction solvent. Without being bound by theory, it is believed that SOLEX is nitrated through an ion-exchange type interaction in the solid state. SOLEX can be prevented from dissolving in, e.g., nitric acid by first loading the nitric acid with $P_2O_5$. In the new process, nitric acid (98+%) is placed into a reactor vessel, and the acid is cooled to about 0-25° C., most preferably to about 15° C. Phosphorus pentoxide is added slowly to the nitric acid with stirring. After the addition of phosphorus pentoxide is complete, SOLEX is poured into the vessel, whereupon nitration begins immediately. Since the SOLEX does not dissolve in this reactant mixture, a solid-state nitration results.

The product can be purified and recovered by repeated washing and filtration. Optionally, the filtrate can be treated with ammonia to generate ammonium nitrate in either solid or liquid form, allowing a recycle loop. Yield of alpha-HMX is usually greater than 95% based on hexamine feed, preferably greater than 99%, most preferably greater than 99.5%. Of the HMX in the reaction product, greater than 95% is the alpha polymorph, preferably greater than 99%, most preferably greater than 99.5%.

The new method for alpha-HMX preparation is shown in reaction 6 (R is methyl in this instance).

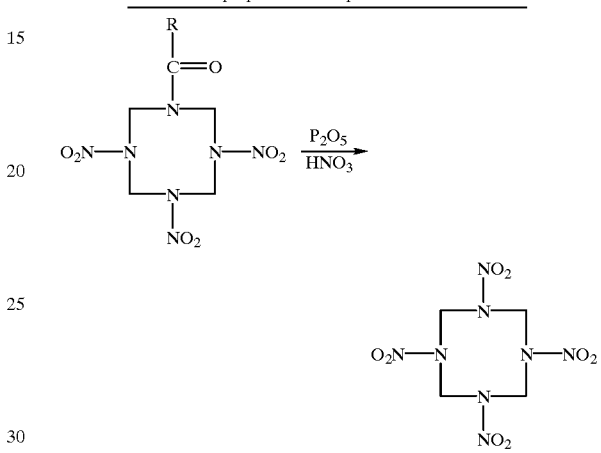

Steps 2C and 2D typically take a total of about 24–48 hours to complete. Because significant amounts of heat are generated, it is preferred to perform these reactions in a plastic (e.g., high density polyethylene) or metal (e.g., aluminum) vessel having a large surface area to enable the heat to be readily dissipated.

Without being bound by theory, it is believed that the ability of the process shown in steps 2A–2D to produce pure (or nearly pure) alpha-HMX results from the ability of SOLEX to form a unique crystal lattice, due to the asymmetric nature of the molecule. The SOLEX can more easily arrange in one polymorphic form because of its pendant acetyl group.

Instead of the procedures in steps 2C and 2D for converting TAT to SOLEX and then to HMX, the alternative procedures of steps 2E and 2F below can be used.

Step 2E: Conversion of TAT to SOLEX

An initial reaction mixture comprising about 75% (by weight) nitric acid and about 25% phosphorus pentoxide is prepared, and TAT is immediately added at a rapid rate. Detectable amounts of SOLEX are produced within 10 minutes. (Pure SOLEX has a melting point of about 225° C.) The reaction is exothermic, and cooling, such as by an external cooling jacket or external cooling coils, should be used to keep the temperature of the reaction mixture below about 68° C., preferably between about 45–55° C. Due to the very fast kinetics of this reaction, the conversion to SOLEX will usually be substantially complete within about two hours. Further conversion of SOLEX to HMX can be avoided by using about one-third more TAT than would be required for complete conversion of TAT to HMX. Alternatively, if it is desired to allow the conversion to process all the way to HMX, stoichiometric amounts of the reactants can be used.

Step 2F: Conversion of SOLEX to HMX.

Nitric acid and SOLEX are combined (preferably in a weight ratio of about 1.5–3.0, most preferably about 1.8), and then a first quantity of phosphorus pentoxide is added. Preferably the weight ratio of the first quantity of phosphorus pentoxide to SOLEX is about 0.25–2.0, most preferably about 0.7–0.8. After about 30 minutes, a second quantity of phosphorus pentoxide can be added, and then after a further 30 minutes, a third quantity of phosphorus pentoxide added. The weight ratio of the first, second, and third quantities of phosphorus pentoxide can suitably be about 4:1:1. A solid-state nitration of the SOLEX occurs, producing HMX in high yield. This reaction usually takes about two hours to be substantially complete. (Pure alpha-HMX has a melting point of about 281° C.)

In this process, preferably the SOLEX is dissolved in the nitric acid, so the reaction takes place in solution.

The HMX composition produced by this method has the useful property of being easily converted to highly pure (e.g., greater than 99% by weight) beta-HMX. As long as the initial HMX composition has a melting point of at least about 277° C., contacting it with a heated organic solvent (e.g., acetone at about 56° C.) will result in the production of the beta polymorph.

In one embodiment of the process, the product is a mixture of various HMX polymorphs.

The procedure of steps 2E and 2F takes much less time than steps 2C and 2D (about four hours total versus about 24–48 hours). In addition, steps 2E and 2F produce less acetyl nitrate byproduct, generate less heat, and require less surface area and/or heat resistance in the reaction vessel.

Optionally, step 2D or 2F can be followed by step 2G.

Step 2G: Recovery of Ammonium Nitrate.

After the nitration has proceeded to the desired extent (e.g., complete conversion to HMX, or alternatively, partial conversion that produces a mixture of HMX and SOLEX), the reaction can be terminated by adding ice water to the reaction mixture, causing the product (e.g., HMX, SOLEX, or a mixture of the two) to precipitate. Filtration can then be used to separate the precipitated product from the remaining aqueous solution. When filtered through a vacuum filter (or any other suitable filter), the product will be retained, and water and impurities will pass into the filtrate. This filtrate, which will be a strong acid solution, can be treated with ammonia to adjust its pH to about 4.0–6.0, preferably about 5.2–5.7. Water is then evaporated by heating it to at least 100° C., preferably to at least about 103° C. Phosphoric acid in the solution will remain liquid at these temperatures. Cooling the filtrate (e.g., to about 70° C. or lower), will cause ammonium nitrate crystals to form. These crystals can be separated from the remaining liquid by conventional methods, and the recovered ammonium nitrate used for fertilizer or other known applications.

The product retained by the initial filtration is then preferably washed with cold water. The wastewater from the cold water wash is a weak acid solution. It can be treated by ion exchange or with activated carbon to remove impurities, allowing the purified water to be recycled.

This step not only minimizes the amount of waste products generated during the manufacturing of HMX, it also produces a highly pure ammonium nitrate byproduct which its itself commercially valuable.

Alternatively, instead of recovering ammonium nitrate, after filtration to remove the solid product, the remaining nitric acid can be concentrated for recycle.

Figure 3:
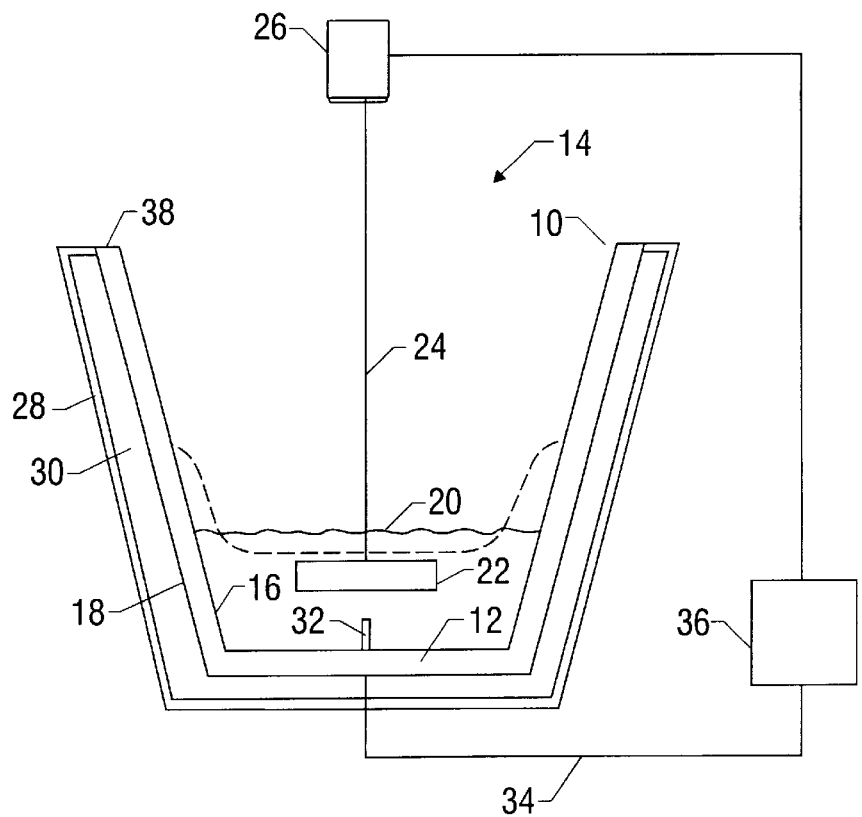
FIG. 3 is an elevational cross-section of a frustoconical reaction apparatus in accordance with the present invention.

Some of the above-described chemical reactions are highly exothermic, and therefore care must be taken to control the temperature of the reaction mixture. This can be done by methods well known to person skilled in this field, using conventional and well-known equipment. However, it is also possible to conduct these reactions in a novel apparatus as shown in FIG. 3.

This particular embodiment of the reaction apparatus comprises a frustoconical vessel 10, which has a closed bottom 12 and an open top 14. The vessel has an inner surface 16 and an outer surface 18. A liquid reaction mixture 20 is located in the vessel, in contact with the inner surface 16. An impeller 22 is mounted on a shaft 24, which can be rotated by a motor 26, thereby stirring the reaction mixture. An external cooling jacket 28 is wrapped around the vessel, in contact with the vessel's outer surface 18. The jacket 28 can contain a heat transfer fluid 30, such as water or Freon, to help remove heat from the vessel 10 and thus from the reaction mixture 20. Enhanced heat removal can be provided by increasing the speed of rotation of the impeller 22. The centrifugal force exerted on the liquid reaction mixture 20 by this faster rotation of the impeller causes the liquid to move outward and up the inner surface 16 of the vessel, whereby the liquid surface takes on the configuration shown by the dotted lines in FIG. 3. As a result of moving some of the liquid up the inner wall of the vessel, the liquid is placed in contact with a greater surface area on the vessel's inner surface 16. As a result, the rate of cooling is increased.

In operation, the higher the rotational speed of the vessel 10, the higher the liquid will be moved up along the inner surface of the impeller, and the greater the rate of cooling. Therefore, by controlling the speed of rotation of the vessel, the temperature of the reaction mixture can be controlled. One preferred way of implementing this control scheme is to place a temperature sensor, such as a thermocouple 32, in the vessel 10, where it will contact the reaction mixture 20. The measurement made by this thermocouple can be transmitted via a wire 34 to a computer 36. The computer can be operationally connected to the motor 26 that drives the shaft 24 and thus the impeller 22. As a result, when the temperature measured by the thermocouple 32 is higher than the preset target temperature, the computer can increase the speed of the motor, thereby increasing the rotational speed of the impeller and moving the liquid further up the inside walls. This increases the cooling rate (due to contacting the liquid with a greater surface area on the cooled inner surface 16), and thus reduces the temperature of the reaction mixture 20. When the temperature has dropped to the desired level, the computer can then slow down the impeller's rotation as needed.

A further enhancement to this control scheme provides for situations where the reaction temperature increases beyond the point where it can be controlled by the available cooling apparatus. If the thermocouple detects that the temperature has exceeded a predetermined alarm level, the computer can then increase the speed of rotation of the impeller enough so that the resulting centrifugal force will expel a predetermined amount (e.g., 20% by weight) of the reaction mixture from the vessel, specifically by rising up the inner walls and going over the top lip 38 of the vessel. This predetermined amount is chosen so that its removal from the vessel 10 will bring the rate of heat generation by the remaining reaction mixture 20 under control. A wide emergency catch pan (not shown in FIG. 3) can be located beneath the vessel, so that the expelled reaction mixture will be contained, and yet will be spread out over a sufficiently large surface area that the reaction rate, and thus the rate of heat generation, will be dampened.

The frustoconical reactor vessel 10 is preferably made of a corrosion-resistant thermoplastic polymer, such as high-density polyethylene or polypropylene. It could alternatively be made of metal, such as aluminum. The impeller 22 and shaft 24 can suitably be made of the same or similar materials. The walls of the cooling jacket can comprise a thermoplastic polymer.

Figure 4:
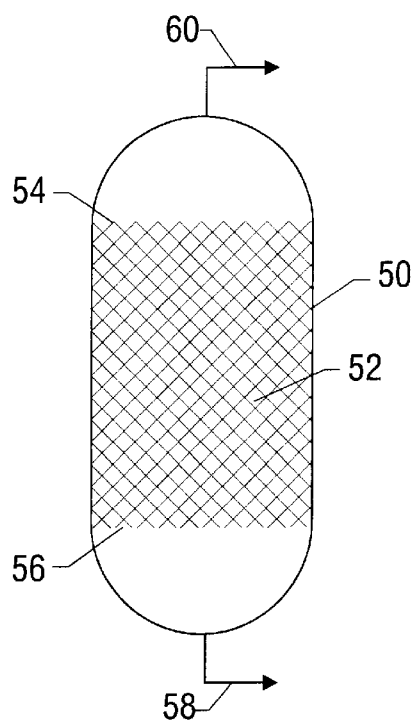
FIG. 4 is an elevational cross-section of a stripper column in accordance with the present invention.

As mentioned above, in some of the process steps, water and volatile impurities can be removed from a reaction product (i.e., from a nitramine or nitramine intermediate) by passing a heated air stream over the product. However, it is also possible to remove such volatile substances by means of a stripper column as shown in FIG. 4.

This separation technique makes use of a stripper column 50, which preferably is packed with saddles, rings, or other suitable packing material 52 well-known in the art. A liquid stream 54 comprising the nitramine or intermediate (e.g., DAPT), water, and usually some relatively volatile organic compounds, is fed into the column somewhere in its upper half. A gas stream 56 that comprises (and preferably consists essentially of) air is fed into the column somewhere in its lower half. The gas stream has a temperature of at least about 120° C., and optionally can have a temperature as high as 200° C. or even higher. The gas and liquid streams are contacted in counter-current fashion within the column, whereby a substantial percentage of the water and volatile organics that are present in the liquid feed stream 54 are removed into the gas phase. A bottoms stream 58 is drawn from the column that contains the nitramine or intermediate (e.g., DAPT) and relatively little water (e.g., less than 10% by weight, preferably less than 5%, most preferably less than 1%). An overhead stream 60 is also drawn from the column, and comprises air, water vapor, and vaporized organic compounds such as formaldehyde and acetic anhydride, and possible also some entrained liquid.

This technique of using a stripper column allows the use of much hotter gas streams than can be used when the gas is merely passed over the surface of a pool of the liquid, while still avoiding or minimizing any degradation of the nitramine or intermediate. Therefore, this technique speeds the drying of the of the desired product. This approach is particularly usefil for drying a DAPT-containing liquor, which can otherwise form a bottleneck in the overall manufacturing process.

Figure 2:
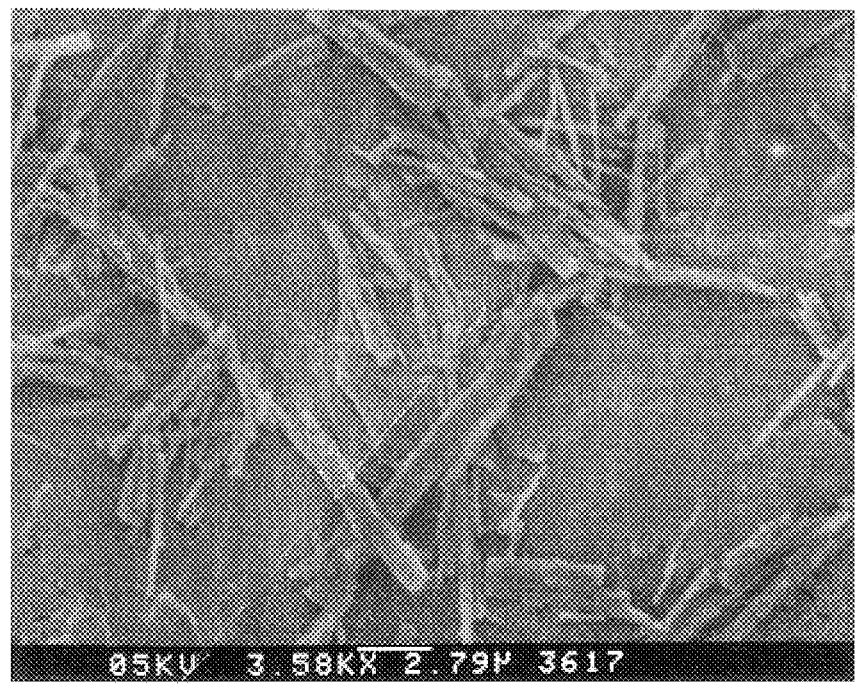
FIG. 2 is a photomicrograph of alpha-HMX particles produced by a prior art process. The white bar at the bottom of the photograph represents a length of 2.79 microns.

The alpha-HMX generated in the above-described processes has a unique crystalline or particulate form consisting of long fibers. Without being bound by theory, it is believed that in some instances, the alpha-HMX particles take the form of elongated, flat sheets that roll up to form tubules having water trapped therein. Whether the particles are hollow or not, they generally are in the form of elongated fibers or rods, having an aspect ratio (length:diameter) of at least about 100:1, often as high as 1,000:1. The novel structure can be seen in FIG. 1, as contrasted to the material in FIG. 2 that was made by a prior art process.

If desired, alpha-HMX can be converted into the beta-form by simply dissolving A-HMX in suitable organic solvent, providing beta-HMX crystals therein, and then evaporating the solvent. Examples of such solvents include acetone, cyclohexane, and a mixture of 20% by weight gamma butyrolactone and 80% acetone.

The alpha-HMX produced as described above has a relatively low bulk density, due to the small diameter and large aspect ratio of the fiber-like particles. This low bulk density makes it difficult to place the material into pressing fixtures. Also, because of the fiber-like structure of the particles, even after being pressed, the bulk density tends not to be close to the maximum theoretical density.

The HMX produced as described herein can be manipulated in several ways to produce useful mixtures, granules, and/or shaped articles that can optionally comprise one or more additional materials. These manipulations can increase the density, structural strength, explosive power, or other properties of the composition. One such manipulation is to coat alpha-H particles with a second material. The term "second material" is used generically herein to refer to materials (or mixtures of materials) other than alpha-HMX that can be combined with it in various ways. Examples of second materials that can be sorbed onto alpha-HMX include RDX, beta-HMX, TNT, ammonium nitrate, aluminum, lithium hydride, and lithium aluminum hydride.

For instance, a first set of alpha-HMX particles can be coated with a second material by sorbing that material on the HMX particles. A second set of alpha-HMX particles can be coated with a second material that is different from the one used to coat the first set of particles. The two sets of coated particles could then be mixed, and pressed into a shaped article. Alternatively, the two sets of coated particles could be made into separate articles or granules, which could then be combined in a single casing.

As yet another alternative, an article or granule made from HMX or coated HMX, which has void spaces therein, can have a second material (or a mixture of such materials) sorbed into those void spaces, and/or sorbed onto the surface of the article or granule.

It would also be possible to sorb multiple layers of different materials onto a HMX-containing particle, granule, or article. The different layers could have, for example, different density, electrical conductivity, etc. The different layers could also be mixtures of HMX with different second materials. Persons skilled in the art will appreciate that these techniques can be used in myriad combinations to produce various particles, granules, and/or shaped articles that comprise at least one second material in addition to alpha-HMX. Such particles, granules, and/or shaped articles will be referred to collectively herein as "HMX products."

One type of HMX product that is especially useful is a granule or shaped article that comprises, and preferably consists essentially of, alpha-HMX and aluminum. The latter provides a large quantity of heat when oxidized, and thus can be highly useful as part of an HMX product.

The alpha-HMX produced as described herein is especially well suited for mixing with aluminum powder, because its unique particulate form allows the ready formation of a highly homogenous mixture. In contrast, prior art beta-HMX tends to form a relatively heterogeneous lid mixture with aluminum powder, thus degrading the explosive power of the beta-HMX rather than enhancing it.

Although a wide variety of aluminum concentrations can be used in such mixtures with alpha-HMX, aluminum concentrations of 0.1–20% by weight are usually preferred. One particularly preferred mixture comprises about 7% aluminum having an average particle size of about three microns. Such a mixture of HMX and aluminum can be granulated or pressed into a shaped article, as described above.

One highly attractive feature of such HMX products that comprise aluminum or some other second material is their structural integrity and strength. Such products can be formed into any desired shape (e.g., a right cylinder, a sphere, or a hollow cone) without the use of a separate binder, which would tend to dilute the energetic properties of the HMX. Although it may be useful to add a small amount of graphite (e.g., less than 1% by weight) to aid in handling, no binder should be required.

One particular method for increasing the bulk density of alpha-HMX involves treating alpha-HMX particles with a small amount of organic solvent (e.g., about 0.3–2.5 g of solvent per g of HMX, preferably about 0.4–0.85 g/g) which at significantly high temperatures (e.g., about 110° C. or higher, preferably about 110–150° C.) dissolves a relatively high mass of HMX per unit mass of solvent. Suitable solvents include gamma butyrolactone, other lactones, acetone, lactams, formamides, TMF, sulfoxides, and fluorocarbons (e.g., Freons). The quantity of solvent is intentionally restricted so that it will dissolve only a fraction (e.g., no more than about 10–20% by weight) of the total HMX so treated. The liquid containing the dissolved portion of the HMX fills at least some of the areas between the remaining undissolved fibers of the alpha-HMX. When the solvent is evaporated, the HMX that had been dissolved is then precipitated out, filling at least some of the voids between the alpha-HMX fibers with solid crystals.

Optionally, seed crystals of another polymorph of HMX can be present (e.g., beta-HMX). The seed crystals can be supplied by small amounts of other HMX polymorphs that may inherently be present as impurities in alpha-HMX. For example, as little as about 1% by weight (or even less) of beta-HMX in a composition that is predominantly (e.g., greater than about 99%) alpha-HMX can be sufficient.

It is also possible to make fine particles of beta-HMX. For example, Class 5 beta-HMX can be made by dissolving HMX (that has been made as described herein) in a solvent such as boiling acetone, and then spray drying using conventional spray drying equipment, e.g., at a temperature of about 50° C.

Without being bound by theory, it is believed that this process for producing fine beta-HMX works well because of the very high purity of the HMX used as the starting material. Class 5 beta-HMX is especially useful as a rocket propellant, and can be made using this technique much less expensively than by the conventional processes for direct synthesis of beta-HMX.

Alpha-HMX particles can be agglomerated into granules having increased bulk density. In particular, the low-density alpha-HMX fibers can be converted to high-density granules, which are suitable for pressing into shaped charges and other durable shaped articles. Finished pressed articles may be prepared from such granules with a very high percent of the theoretical maximum density. No binders or additives of any kind are required.

After drying the alpha-HMX, the mass of material is broken down into particulates having a desired size distribution. The desired size distribution can be effected by passing the starting material through a sieve. The sieved particulate material is then "dry stirred." This is preferably done by stirring the particulates in a circular motion in the presence of a small amount (e.g., 0.001–0.5 g of solvent per g of HMX) of additional solvent that helps fluidize the entire mass. The quantity of solvent is less than what would cause the material to cake, because caking would prevent the fluid motion of the particles. A plurality of particulates agglomerates to form a granule. In general, the smaller the particulates, the smaller the granules that will be formed. The fluidized motion of the solvent dampened particles causes the further compaction and rounding of each granule. During the stirring process, additional small amounts of solvent may be added to the moving bed of material, further softening the material and assisting the dynamic actions which promote the formation of generally spherical HMX granules having increased bulk density. This process preferably is carried out by circulating the sieved material in a circular or elliptical channel in a vessel, so that centrifugal force helps cause the particles to agglomerate into denser granules. These granules are porous and permeable. Therefore, one or more second materials can be sorbed into the granules. It is also possible to coat the exterior of a granule with one or more second materials. Further, a plurality of granules can be formed into an article having any desired shape, for example by pressing. The alpha-HMX granules in combination with one or more second materials will form an article that will retain its shape under normal handling, without the need for any binder or adhesive.

HMX, and compositions containing Hi together with other materials, have many uses as explosives or propellants. For example, the oil industry uses HMX as an explosive in shaped charges for the perforation of well casings. Apparatus and techniques for using such shaped charges for perforation are well known. Examples of such perforation equipment and techniques are described in the following Schlumberger U.S. patents, each of which is incorporated here by reference: U.S. Pat. Nos. 5,911,277; 5,673,760; 5,597,974; 5,505,134; and 5,355,802.

The various aspects of the present invention can be further understood from the following examples.

EXAMPLE 1

(Preparation of DAPT)

An open-top, 8-quart stainless steel pot equipped with an efficient mechanical stirrer is charged with 980 grams (7 moles) of hexamine. Water (980 grams) is added to dissolve much of the hexamine. This hexamine/water slurry is cooled to approximately 0° C. To this, 490 grams of ice are then added. Acetic anhydride (530 grams, slightly more than 2 moles) is then poured into the reaction vessel with rapid stirring over a period of about 30 seconds. The reaction is evidenced by the rapid melting of the ice in the reaction mixture. The reaction is finished within a minute or so after the acetic anhydride is added, and the product is ready for recovery and/or purification.

Purification of the product can be accomplished by passing steam over the reaction product in the reaction vessel. This heats the material and causes the acetic acid by-product to evaporate. Another by-product, a formaldehyde polymerization by-product, is also formed. To remove this polymer by-product and any remaining water, acetic acid, or other volatile material, the reaction mixture is heated to 130–140° C. for 20–30 minutes. The product is then cooled. DAPT can be isolated and recovered at this point by filtration, washing, and drying. The typical yield is 65–100%.

EXAMPLE 2

(Conversion of DAPT to TAT)

To 1482 g of cooled and purified DAPT, 1570 grams of acetic anhydride is added with rapid stirring. Careful control of cooling must be maintained in order to keep the system below reflux temperature (138° C.). After the initial exotherm, the temperature is kept at roughly 110–120° C. for 2 hours. Conversion of DAPT to the ester intermediate (having three acetyl groups in addition to the one ester group) is complete at this point.

Conversion of the ester to TAT (i.e., the tetraacetyl derivative) is accomplished by the addition of a catalytic amount (preferably less than five mole percent) of transition metal oxides, and the addition of 126 grams (7 moles) of water. A combination of copper oxide and iron oxide is preferred for use as a catalyst in the reaction. The copper can be added in the form of copper wire, while the iron can be added in the form of steel wool. More water (1 mole per mole of hexamine in the DAPT, as opposed to isolated hexamine) is then added to the reaction mixture over a period of approximately 90 minutes. The temperature is then increased to 130–140° C. for 20–30 minutes, driving off any residual acetic acid, any remaining water, and other volatiles. The ester functionality is hydrolyzed, generating a primary alcohol and acetic acid. The alcohol quickly decomposes to generate formaldehyde, which leaves the reaction mixture as a gas. The product formed is a secondary amine, which then reacts with a second mole of acetic anhydride to form TAT.

TAT is isolated by placing the system in a rapidly flowing stream of air, with heating, which causes the volatile components to be removed. Once all volatile components have been removed, the temperature of the system will rapidly rise and should be allowed to reach 140–150° C. The heat is then removed from the system, but airflow should remain on, in order to cool the system. Once the system reaches 70–90° C., acetone should be added (enough to increase the volume by about 20%), followed by a few milligrams of seed TAT crystals to facilitate crystallization. The crystallized product is then filtered, and washed with cool acetone. The crystalline product is then dried at 1 00° C. (removing any remaining water), and stored in an airtight container to prevent absorption of water. A quantitative yield of product is recovered as a solid.

EXAMPLE 3

(Preparation of AAHT)

Hexamine is dissolved in a minimum of water (1:1 molar ratio) which is then cooled to ≦10° C. A mass of ice equal to ⅓ the mass of hexamine is pre-cooled to about −30° C. This is then mixed with the pre-cooled hexamine solution, creating a slurry. To this slurry, 2 mole equivalents of acetic anhydride (also pre-cooled to −30° C.) are added. AAHT is formed within a minute, as is evidenced by the immediate melting of the ice, illustrating the exothermic nature of this reaction.

Purification of AAHT is accomplished by heating the reaction vessel to a temperature above 130° C. in the presence of flowing air. This has the effect of driving off all volatile components, leaving the AAHT. The evaporation optionally can be done in a two-stage evaporation, as described above for recovery of DAPT. The AAHT can be isolated at this point or the synthesis can continue.

EXAMPLE 4

(Alternative preparation of AAHT)

AAHT can also be produced utilizing hexamine hexahydrate (referred to hereafter as hex—hex).

One mole of hexamine is placed into 6 moles of water at room temperature. This mixture is then cooled to approximately −30° C., forming hex-hex, a waxy solid that can be isolated and is quite stable.

For AAHT synthesis, a quantity of hex-hex is cooled to −30° C., followed by the addition of slightly more than 2 mole equivalents anhydride. The anhydride is also pre-cooled to approximately −30° C. before addition. There is a slow onset to the reaction, until it reaches approximately −15° C. at which point a rapid rise in temperature occurs, bringing the reaction to approximately 40–50° C. Purification is accomplished in the same manner as in Example 4.

EXAMPLE 5

(Conversion of AAHT to TAT)

Three moles of acetic anhydride are added per mole of AAHT, and the reaction mixture is then heated to 110–120° C. and stirred for 2 hours, completing synthesis of the diester. Removal of volatile components by evaporation allows isolation of the diester.

Alternatively, instead of recovering the diester, it can be converted to TAT in situ as follows. The reaction mixture containing the diester is allowed to cool to room temperature (about 22° C.), and iron and copper oxide catalysts are added in the form of steel wool and copper wire. Special care must be taken to leave the reaction vessel uncovered so that the formaldehyde generated during the course of the hydrolysis can escape. Two moles water per mole of diester are then added over a period of about 90 minutes, at which point the hydrolysis is complete. The product, TAT, is purified by heating to 130–150° C. under an airjet for a period of approximately 20 to 45 minutes, which evaporates the acetic acid byproduct and any water that is coordinated to the TAT. The typical yield is 90–100%.

EXAMPLE 6

(Conversion of TAT to SOLEX)

To generate 100 grams of SOLEX, 150 grams of nitric acid (a five-fold reduction over the prior art method) is placed into an aluminum or plastic reactor. The reactor temperature is adjusted to 15° C. Crystalline TAT (100 grams) is slowly added to the reaction vessel with efficient stirring. After the TAT has dissolved into the nitric acid, 24 grams of phosphorus pentoxide is added. Care is taken to insure that the rate of stirring is sufficient to prevent clumping of the reagents; clumping can cause localized overheating, a potential hazard. The reaction is then stirred for about 1 hr, at which point 8 additional grams of phosphorus pentoxide is added. Time lapses between additions of phosphorus pentoxide allow the heat of reaction to dissipate. The addition is repeated two more times, until a total of 48 grams of phosphorus pentoxide has been added. This is a dramatic decrease in the amount of phosphorus pentoxide required by prior methods. The reaction temperature is kept between 20–25° C. during the course of the reaction. After the addition of phosphorus pentoxide is complete, the reaction is stirred for approximately 5 hours until the reaction mixture begins to gel. At this point, the reaction is nearly finished and the reaction mixture is transferred to a temperature-controlled container and allowed to stand for 24–48 hours at room temperature. Purification is accomplished by filtering the material and washing it with copious amounts of hot water. The result of this process is a nearly quantitative yield of pure SOLEX.

EXAMPLE 7

(Alternative conversion of TAT to SOLEX)

First 562.5 g of P2O5 are dissolved in 1,125 ml of nitric acid. Next 500 g of TAT are added in four increments of 125 g each, with 30 minutes between each addition of TAT. The reaction mixture is maintained at about 30–45° C., preferably at about 37° C. The typical yield of SOLEX is well in excess of 90% (e.g., about 96%).

EXAMPLE 8

(Conversion of SOLEX to alpha-HMX)

To prepare 100 grams of HMX, 100 ml of nitric acid is added to an aluminum or plastic reactor. The contents of the vessel are cooled to approximately 15° C. 80 grams of phosphorous pentoxide are slowly added with stirring to the reactant mixture in the vessel, resulting in a temperature increase due to the exothermic formation of dinitrogen pentoxide. The rate of addition should be monitored to allow no more than a 10–20° C. increase in temperature. After the addition of the phosphorus pentoxide, the reaction vessel should be cooled to 10–20° C. After the addition of the phosphorous pentoxide is complete, 100 grams of SOLEX is rapidly stirred into the mixture, generating a viscous slurry. Care needs to be taken to ensure that the entire mixture is cooled, which is necessary to avoid the possibility of a fume-off. The mixture will continue to thicken during this time, so the mixture should be transferred to an aging container that has enough cooling surface to permit cooling without stirring. The mixture immediately begins to thicken. The reactant mixture is then transferred to a suitable container having temperature control apparatus.

After aging for 24–48 hours, at room temperature, the reacted material is filtered and washed several times with fresh (deionized) hot water in a vacuum filter. This process should be repeated several times in order to insure complete purification. A quantitative yield of high purity alpha-HMX is obtained as a solid.

EXAMPLE 9

(Alternative conversion of SOLEX to HMX)

First, 600 g of SOLEX are dissolved in 1,091 ml of nitric acid. To this mixture, 436.3 g of $P_2O_5$ are added. After waiting 30 minutes, another 109.1 g of $P_2O_5$ are added. After waiting another 30 minutes, another 109.1 g of $P_2O_5$ are added. The temperature of the reaction mixture is maintained at about 30–45° C., preferably at about 37° C. The reaction is complete within about five hours, and the yield of HMX is usually about 95% or greater.

EXAMPLE 10

(Conversion of alpha-HMX to beta-HMX)

The HMX product of Example 9, after being washed with water and dried, is a fluffy powder having a melting point of at least about 277° C. To 100 g of this HMX are added 300 ml of acetone at a temperature of about 56° C. The HMX converts to beta-HMX within about five minutes.

EXAMPLE 11

(Adsorption of substrate onto alpha-HMX)

TNT is dissolved in ethyl acetate or some other solvent. Either the solvent should be one in which HMX will not dissolve, or else the solvent should be substantially presaturated with TNT. The TNT solution is then contacted with alpha-HMX made as in Example 8. Drying causes the TNT to form a thin film or coating on the HMX. The amounts of TNT and HMX used can vary widely, but can suitably be, for example, 1:1 ratio by weight.

EXAMPLE 12

(Granulation of alpha-HMX)

A quantity of alpha-HMX (400 g) is treated with a mixed solvent (235 g of 20% gamma butyrolactone, 80% acetone). To the resulting paste is added with stirring a small quantity (1.6 g) of fine beta HMX seed crystals. The stirring is not elaborate and is complete in a few minutes. The resulting paste is placed as a shallow layer into a pan and the pan is placed in an oven at about 120–130° C. The paste is removed when dry in about 20 minutes. The dried paste is broken up and passed through a screen, e.g., a #14 sieve. The resulting powder is transferred to an agitator consisting of a cylindrical chamber with a stirrer or impeller. The particles are stirred so the whole bed is in motion and is flowing, fluidized but not violently so, and as the mixture is flowing a small amount of the solvent (e.g., 0.05 g of solvent per g of particulates) is added. The quantity of solvent is limited only by the fact that too much (e.g., about 10 g) will cause the particles to cake. The break point between acceptable and excessive amounts of added solvent is rather sharp (e.g., plus or minus a few drops of solvent). The material is treated in this manner for a few minutes, after which the material is removed from the agitator and dried in an oven at about 90° C.

EXAMPLE 13

(Crystallizing beta-HMX in alpha-HMX voids)

HMX prepared as in Example 9 is dissolved in a solvent such as acetone. This solution is contacted with porous alpha-HMX particles made as in Example 8. Evaporation of the solvent causes crystallization of beta-HMX in the void spaces in the alpha-HMX particles.

The preceding description of specific embodiments of the present invention is not intended to be a complete list of every possible embodiment of the invention. Persons skilled in this field will recognize that modifications can be made to the specific embodiments described here that would be within the scope of the present invention.

What is claimed is:

1. A process for preparing an HMX product, comprising the steps of:
    (a) providing a granule that comprises a plurality of alpha-HMX particles and which has internal void spaces; and
    (b) sorbing at least one second material into the void spaces in the granule.

2. The process of claim 1, wherein the second material is sorbed into the granules by using a vacuum to draw a gas phase comprising the second material into the granule.

3. The process of claim 1, wherein the second material is sorbed into the granules by:
    (c) mixing the second material with a liquid solvent;
    (d) contacting the solvent with the granules; and
    (e) evaporating the solvent, whereby the second material is sorbed into the granules.

4. The process of claim 3, wherein the solvent is an organic solvent.

5. The process of claim 1, wherein the second material is an energetic material.

6. The process of claim 5, wherein the energetic material is selected from the group consisting of beta-HMX, RDX, TNT, ammonium nitrate, and mixtures thereof.

7. The process of claim 1, wherein the second material is a fuel.

8. The process of claim 7, wherein the fuel is selected from the group consisting of aluminum, lithium hydride, lithium aluminum hydride, and mixtures thereof.

9. The process of claim 1, further comprising coating the exterior of the granule with a second material.

10. The process of claim 9, wherein the second material coated on the exterior of the granule is the same as the second material sorbed into the granule.

11. The process of claim 9, wherein the second material coated on the exterior of the granule is different than the second material sorbed into the granule.

12. The process of claim 9, wherein a plurality of coatings are applied to the exterior of the granule.

13. The process of claim 1, wherein a mixture of at least two second materials are sorbed into the granule.

14. A process for preparing an HMX composition, comprising the steps of:
   (a) contacting alpha-HMX granules having void spaces therein with an solvent in an amount from about 0.1–2.5 g of solvent per g of alpha-HMX, whereby a fraction of the HMX is dissolved;
   (b) providing beta-HMX crystals in the dissolved HMX; and
   (c) evaporating the solvent, whereby beta-HMX is deposited in void spaces of undissolved alpha-HMX particles.

15. The process of claim 14, wherein the solvent is an organic solvent.

16. The process of claim 14, wherein the organic solvent is selected from the group consisting of acetone, cyclohexane, gamma butyrolactone, and mixtures thereof.

17. The process of claim 14, wherein the beta-HMX crystals are provided as part of the alpha granules.

18. The process of claim 17, wherein the beta-HMX crystals comprise less than 1% by weight of the alpha-HMX granules.

19. The process of claim 18, wherein the weight ratio of beta-H to alpha-HMX in step (b) is at least 1:1.

20. The process of claim 14, wherein the beta-HMX crystals are providing by adding them to the solvent from an external source.

21. The process of claim 14, wherein the amount of beta-HMX crystals provided in step (b) is no greater than about 1.0% by weight of the alpha-HMX.

22. The process of claim 21, wherein the weight ratio of beta-HMX provided in step (b) to alpha-HMX is at least 1:1.

23. The process of claim 14, wherein about 10–20% by weight of the alpha-HM is dissolved in step (a).

24. The process of claim 14, further comprising the step of pressing the product of step (c) into a shaped article.

* * * * *